United States Patent
Giorgetti

(10) Patent No.: US 9,707,198 B2
(45) Date of Patent: Jul. 18, 2017

(54) COMPOSITIONS COMPRISING AMINO ACIDS FOR USE IN THE TREATMENT OF STROKE IN PATIENTS WITH DYSPHAGIA

(71) Applicant: PROFESSIONAL DIETETICS S.p.A., Milan (MI) (IT)

(72) Inventor: Paolo Luca Maria Giorgetti, Milan (IT)

(73) Assignee: Professional Deitetics S.p.A., Milan (MI) (IT)

( * ) Notice: Subject to any disclaimer, the term of this patent is extended or adjusted under 35 U.S.C. 154(b) by 0 days.

(21) Appl. No.: 14/878,100

(22) Filed: Oct. 8, 2015

(65) Prior Publication Data

US 2016/0101078 A1    Apr. 14, 2016

(30) Foreign Application Priority Data

Oct. 8, 2014 (IT) ............................... TO2014A0806

(51) Int. Cl.
| | | |
|---|---|---|
| *A61K 31/198* | (2006.01) | |
| *A61K 31/405* | (2006.01) | |
| *A61K 31/4172* | (2006.01) | |
| *A61K 31/51* | (2006.01) | |
| *A61K 31/675* | (2006.01) | |

(52) U.S. Cl.
CPC .......... *A61K 31/198* (2013.01); *A61K 31/405* (2013.01); *A61K 31/4172* (2013.01); *A61K 31/51* (2013.01); *A61K 31/675* (2013.01)

(58) Field of Classification Search
CPC .................................................. A61K 31/198
USPC ............................................................ 514/89
See application file for complete search history.

(56) References Cited

FOREIGN PATENT DOCUMENTS

| JP | 2012-201625 A | 10/2012 |
| WO | 2012/133198 A1 * | 10/2012 |
| WO | 2012/142678 A1 | 10/2012 |

OTHER PUBLICATIONS

Listed on the European Search Report filed by applicant on Mar. 8, 2016.*
Extended European Search Report dated Jan. 29, 2016, issued in European Application No. 15187946.7.
International Search Report and Written Opinion of the International Searching Authority mailed Feb. 4, 2016, issued in International Application No. PCT/IB2015/057662.
Druml, Wilfred, et al., "Amino acid kinetics in patients with sepsis," The American Journal of Clinical Nutrition, 2001, vol. 73, pp. 908-913.

* cited by examiner

*Primary Examiner* — Taofiq A Solola
(74) *Attorney, Agent, or Firm* — Nixon & Vanderhye P.C.

(57) ABSTRACT

Composition for use in the treatment of stroke, particularly in patients with dysphagia, the composition comprising an active agent, said active agent comprising the amino acids leucine, isoleucine, valine, lysine, threonine and at least one of histidine, phenylalanine, methionine, tryptophan, tyrosine, cystine. The composition further comprises one or more thickener agents in an amount between 10% and 50% by weight, more preferably between 20% and 30% by weight, with respect to the active agent weight.

12 Claims, 3 Drawing Sheets

Fig. 3
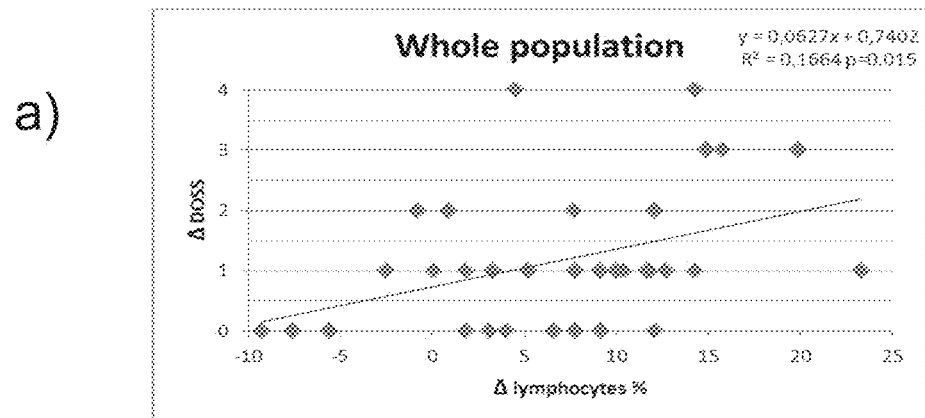
a)
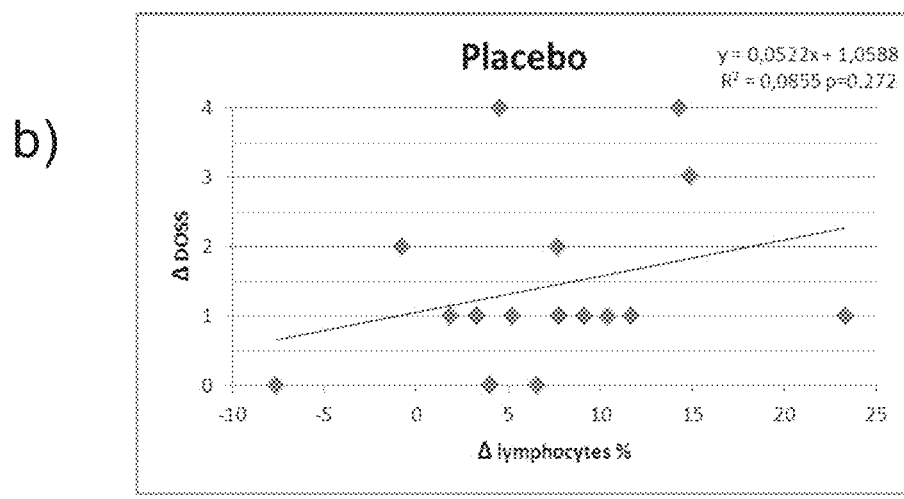
b)
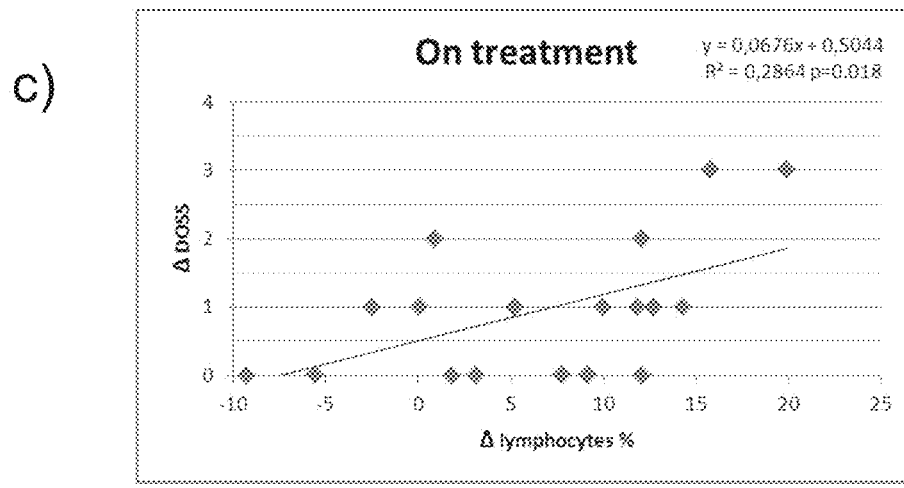
c)

COMPOSITIONS COMPRISING AMINO ACIDS FOR USE IN THE TREATMENT OF STROKE IN PATIENTS WITH DYSPHAGIA

This application claims priority to IT Patent Application No. TO2014A000806 filed Oct. 8, 2014, the entire content of which is hereby incorporated by reference.

FIELD OF THE INVENTION

The present description relates to compositions for use in the treatment of stroke in patients, particularly patients with dysphagia.

BACKGROUND

Strokes are the world's leading cause of disability. About one-third of stroke survivors are permanently disabled one year after the acute event. About two-thirds of patients do not completely recover after strokes, while one-third cannot walk without assistance. Furthermore, in hemi-paretic subjects, who can still walk, gait efficiency is reduced and the energy cost of the gait is increased compared with efficient symmetric gait. In addition to the loss of central trophic effects and transynaptic degeneration of lower motor neurons, post-stroke skeletal muscle changes can also potentially contribute to disability. These changes include fibre-type shift in the paretic (=contro-lateral) side, increased intra-muscular fat (myosteatosis) substituting muscle tissue, spasticity, disuse, malnutrition and muscle unloading. Previous study showed that skeletal muscles of sub-acute stroke patients are subject to a persistent systemic inflammatory state, which could lead to hypercatabolism (i.e. protein degradation is higher than protein synthesis). This inflammatory state of the unaffected side could contribute to patient disability by inducing a loss of both muscle mass and strength, which leads to patient disability. This problem is particularly relevant in dysphagic patients. Therefore, the need exists to identify new compositions able to reduce the above mentioned problem.

SUMMARY OF THE INVENTION

The present description has the aim of providing compositions, for use in the treatment of stroke in patients, particularly patients with dysphagia, which are able to attenuate the above mentioned persistent systemic inflammatory state, and hence attenuate or even convert muscle hypercatabolism (MH) to balanced protein turnover or anabolic activity muscle anabolism.

Before consumption, the compositions herein described are dispersed in a liquid, preferably water, which acquires the ideal viscosity and consistency for the ingestion by a patient with dysphagia.

According to the present description, the above object is achieved thanks to the subject matter recalled specifically in the ensuing claims, which are understood as forming an integral part of this disclosure.

An embodiment of the present description provides a composition for use in the treatment of systemic inflammatory state associated to stroke in patients, particularly patients with dysphagia, the composition comprising an active agent, the active agent comprising the amino acids leucine, isoleucine, valine, lysine, threonine and at least one of the amino acids histidine, phenylalanine, methionine, tryptophan, tyrosine, cystine, the composition further comprising one or more thickener agents in an amount between 10% and 50% by weight, more preferably between 20% and 30% by weight, with respect to the active agent weight.

The thickener agents may be selected among xanthan gum, methylhydroxypropylcellulose, konjak gum, konjak glucomannan, gum Arabic (Acacia gum), modified starches.

The presence of such agents in the composition allows to thicken the liquid, preferably water, wherein the composition is dispersed before consumption.

In some embodiments, the composition herein disclosed further comprises vitamins, preferably selected in the group of vitamins B, such as vitamin $B_1$ and/or vitamin $B_6$.

In a further embodiment, the composition also includes carbohydrates, additives and/or flavouring substances.

The Inventor found that the compositions herein disclosed are able to convert muscle hypercatabolism to anabolism of the ipsilateral (unaffected) arm of disphagic stroke subjects. In this way a better recovery of physical autonomy may occur.

A further embodiment of the present description provides a composition for use in the treatment of a systemic inflammatory state, the composition comprising an active agent, the active agent comprising the amino acids leucine, isoleucine, valine, lysine, threonine and at least one of the amino acids histidine, phenylalanine, methionine, tryptophan, tyrosine, cystine.

An advantage linked to the use of the compositions described herein lies in the high tolerability of the compositions, which can be administered chronically. In a preferred embodiment, the administration may occur over a period sufficiently long to allow at least partial recovery of stroke.

Another advantage linked to the use of the composition described herein lies in the fact that the use of amino acids in free form comprised in the active agent allows producing such compositions at a comparatively extremely low cost with respect to proteins and growth factors synthesis, through per se known production processes and widely used in the field of preparing compositions based on free amino acids. The field of application of the invention may however also be extended to amino acids obtained through genetic engineering or any other artificial method.

BRIEF DESCRIPTION OF THE DRAWINGS

The invention will now be described, by way of example only, with reference to the enclosed figures, wherein:

FIG. 3 represents the relationship between overtime changes of peripheral blood lymphocytes as % total white cells and deglutition ability (DOSS) in all stroke population (panel a), in subjects on placebo (panel b) and on essential amino acid treatment (panel c). The number of dots appearing in the plots is lower than the real number of study patients because of the overlapping of values in some cases.

DETAILED DESCRIPTION OF PREFERRED EMBODIMENTS

Figure 1:
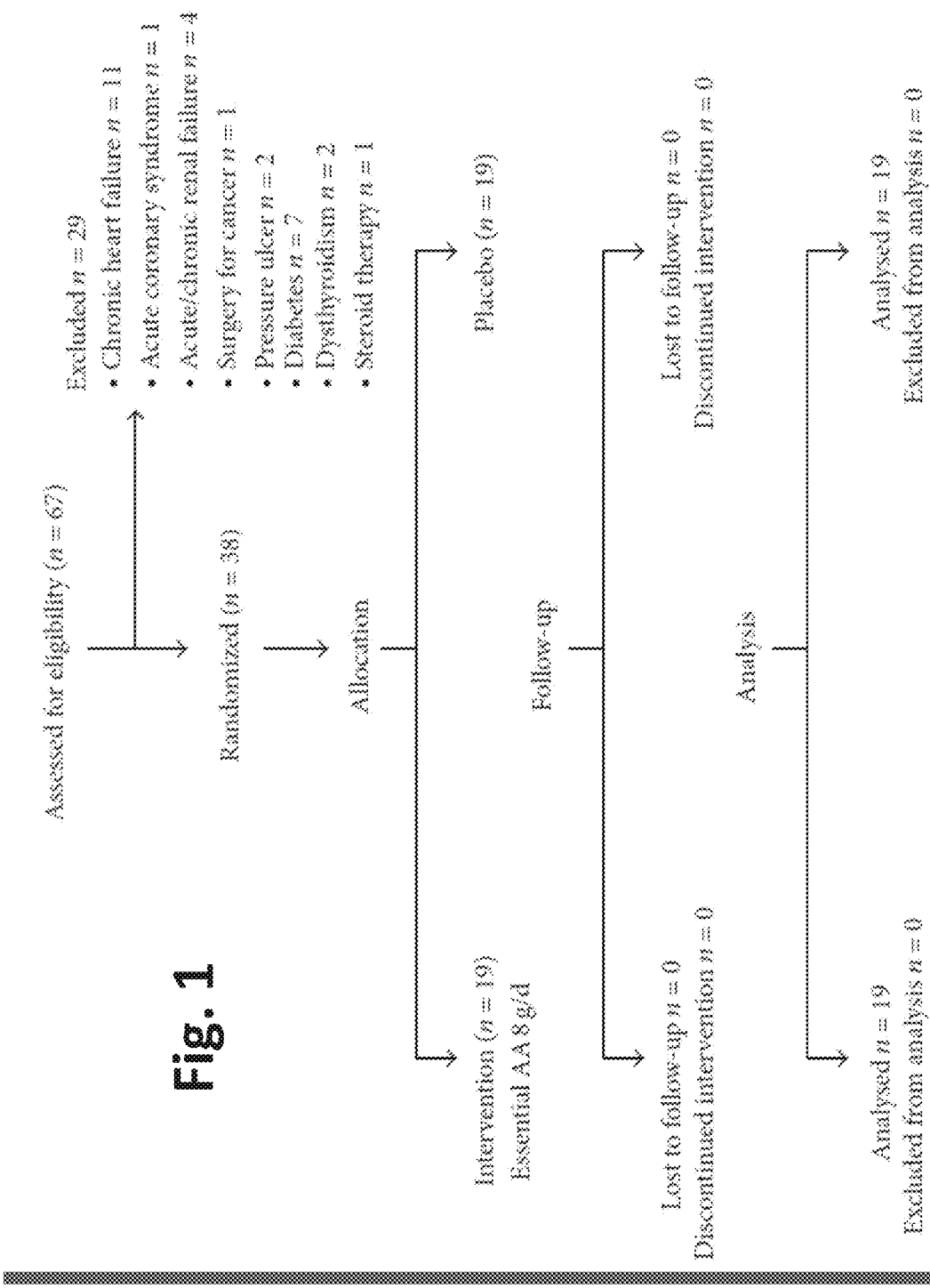
FIG. 1 is a flow diagram of a trial supplementation with the composition herein described versus placebo during the treatment of dysphagic stroke patients. The diagram includes the number of patients analyzed for the main outcome (unaffected arm muscle hypercatabolism)

In the following description, numerous specific details are given to provide a thorough understanding of embodiments.

The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the embodiments.

The composition for use in the treatment of stroke in patients with dysphagia, namely systemic inflammation state associated to stroke, herein disclosed comprises an active agent, the active agent comprising the amino acids leucine, isoleucine, valine, lysine, threonine and at least one of the following amino acids histidine, phenylalanine, methionine, tryptophan, tyrosine, cysteine. The composition further comprises one or more thickener agents in an amount between 10% and 50% by weight, more preferably between 20% and 30% by weight, with respect to the active agent weight.

The thickener agents may be selected among xanthan gum, methylhydroxypropylcellulose, konjak gum, konjak glucomannan, gum Arabic (Acacia gum), modified starches. The presence of such agents, preferably xanthan gum ormethylhydroxypropylcellulose, allows to thicken the liquid, preferably water, wherein the composition is dispersed before consumption.

It is known that people with dysphagia generally lack proper muscle control and coordination to properly seal the windpipe or they lack the ability to properly propel the entire bolus of food and/or beverage to the stomach. It is therefore extremely important that the foodstuffs dysphagic patients consume have the proper viscosity and consistency.

Once the composition herein disclosed is dispersed in a liquid, preferably water, the consistency of the resulting product has the ideal viscosity for the ingestion by a patient with dysphagia.

In some embodiments, the one or more thickener agents are present in an amount between 2% to 30%, preferably between 4% to 15% by weight of the dry weight of the composition.

After preparation, the dispersion is allowed to rest for 5 minutes at room temperature in order to obtain the desired consistency and viscosity.

The amount of liquid to add to the composition herein disclosed will depend, for example, on the consistency that is necessary to obtain. This parameter will be evaluated and determined by a person skilled in the field also taking into account the degree of dysphagia of the patient.

In one or more embodiments, the composition may be added to the liquid, preferably water. The chosen concentration depends on the consistency of the gel to be obtained.

In some embodiments, the composition herein disclosed further comprises vitamins, preferably selected in the group of vitamins B, such as vitamin $B_1$ and/or vitamin $B_6$. In a further embodiment of the present disclosure, the composition also includes carbohydrates, additives and/or flavouring substances.

Preferred carbohydrates may be selected among maltodextrins. The additive may be selected among sodium citrate tribasic dehydrate, aspartame powder, acesulfame potassium, sucralose. A preferred flavouring substance is banana flavour.

According to some embodiments of the present disclosure, the preferred isoleucine:leucine weight ratio is comprised in the range 0.2-0.7, preferably between 0.4-0.6 and/or the preferred valine:leucine weight ratio is comprised in the range 0.2-0.8, preferably in the range 0.4-0.7.

In a further embodiment, the threonine:leucine weight ratio is comprised in the range of 0.15-0.50, preferably between 0.20-0.45 and/or the lysine:leucine weight ratio is comprised in the range of 0.15-0.60, preferably between 0.30-0.55.

In another embodiment, the leucine:isoleucine:valine weight ratio is equivalent to 2:1:1.

In a further embodiment, considering the sum of leucine, isoleucine, valine, threonine and lysine equal to 1, then the overall amount of the further essential amino acids may vary between 0.02 to 0.25 (i.e. 1:0.02-0.25), preferably from 0.05 to 0.15 (i.e. 1:0.05-0.15), still intended as the weight ratio.

In a further embodiment, cysteine is present in an weight amount comprised between 150% and 350% of methionine.

In some embodiments, the active agent comprises the non-essential amino acid tyrosine in an amount comprised between 15 and 50%, preferably between 20 and 35%, of the weight amount of phenylalanine.

In a further embodiment, the active agent consists of the amino acids leucine, isoleucine, valine, lysine, threonine in combination with histidine, phenylalanine, methionine, tryptophan, tyrosine, cystine and the composition further comprises one or more thickener agents in an amount between 10% and 50% by weight, more preferably between 20% and 30% by weight, with respect to the active agent weight.

In some embodiments, the composition may also be administered to stroke patient without dysphagia for the treatment of the systemic inflammation state associated to stroke. In such cases, the composition may comprise the active agent (leucine, isoleucine, valine, lysine, threonine and at least one of histidine, phenylalanine, methionine, tryptophan, tyrosine, cystine) without thickening agents.

In further embodiments, the composition may be administered for use in the treatment of a systemic inflammatory state, the composition comprising an active agent, the active agent comprising the amino acids leucine, isoleucine, valine, lysine, threonine and at least one of the amino acids histidine, phenylalanine, methionine, tryptophan, tyrosine, cystine.

Furthermore, in particular, when preparing the compositions according to the instant disclosure, and specifically the active agent, the amino acids serine, proline, glycine, alanine, glutamic acid and, above all, arginine are preferably avoided, given that they can be counterproductive or even harmful in some concentrations or stoichiometric ratios with the said formulation.

The amino acids indicated above can be replaced by respective pharmaceutically acceptable derivatives, namely salts.

Preferably, the composition is in the form of a dry powder and, in order to be administered to the patient it is dispersed in a liquid, preferably water.

Further specifications, in terms of amounts and ratios among the various amino acids provided for by the compositions for use in the treatment of stroke in patients with dysphagia are contained in the attached claims, which form an integral part of the technical teaching provided herein in relation to the invention.

The results herein provided show that muscle protein metabolism of the unaffected arm of dysphagic sub-acute stroke individuals could be characterized by MH which can be corrected by the administration of the composition herein described.

EXAMPLE 1

Material and Methods

Population. Sixty-seven dysphagic sub-acute stroke patients (<3 months after acute cerebrovascular event) (Guidelines of the Ministry of Health for rehabilitation activities. National Health Plan 1998-2000) admitted to our rehabilitation centre were eligible for the study. 11 subjects were excluded due to associated chronic heart failure, 1 for acute coronary syndrome, 4 for acute or chronic renal failure (creatinine clearance<30 mg/100 ml), 1 for cancer surgery, 2 for pressure ulcer, 7 for diabetes (on oral hypoglycemic or insulin treatment), 2 for dysthyroidism and finally 1 for being on steroid therapy. The reason for excluding these diseases was strictly related to their strong impact on muscle protein metabolism.

The remaining thirty-eight patients (29 males+9 females; 69.7±11.4 yrs) were enrolled in this randomized, double blind, placebo-controlled study. The reason for patient admission was due to rehabilitation for dysphagia and hemiplegia. All patients were bedridden and had been admitted from neurosurgery (34.2%), neurological or stroke units (52.6%) or other rehabilitation settings (13.2%). Cerebrovascular accident documented by computerized tomography was ischemic in 57.9% or haemorrhagic injury (42.1%). Ischemic and haemorrhagic individuals were pooled because, in the rehabilitative phase of stroke, these two groups have similar metabolic, nutritional, functional profiles (Aquilani et al., 2014).

On the basis of computerized tomography or magnetic resonance imaging, the damaged stroke areas were classified in relation to the location of the ischaemic distruction as PACI (partial anterior circulation infarction; 23.7%), TACI (total anterior circulation infarction; 50%) or POCI (posterior anterior circulation infarction; 26.3%). These data are contained in Table 1, which also shows stroke severity and assessed mechanisms underlying swallowing abnormalities.

TABLE 1

|  | Patients (%) |
|---|---|
| Stroke location | |
| Cortical stroke: | |
| Dominant (left) | n°9 (23.7%) |
| Nondominant (right) | n°8 (21%) |
| Subcortical stroke: | |
| Dominant (left) | n°7 (18.4%) |
| Nondominant (right) | n°5 (13.2%) |
| Brainstem stroke | n°6 (15.8%) |
| Cerebellar stroke | n°3 (7.9%) |
| Stroke severity | |
| FIM impairments (score): | Motor 21 ± 15* |
|  | Cognitive 8 ± 6.5* |
| Dysphagia (clinical/videofluoroscopic evaluation) | |
| Delayed oral transit | n°18 (47.4%) |
| Incomplete oral clearance | n°10 (26.3%) |

TABLE 1-continued

|  | Patients (%) |
|---|---|
| Wet voice | n°3 (7.9%) |
| Absent cough | n°7 (18.4) |

At admission, all patients were fed via percutaneous endoscopy gastrostomy (PEG; n=30) or by oral modified diet (n=8).

Procedures. Within two days of admission, after overnight fasting at 8 am, blood samples were taken from each patient to determine the following:

1) Plasma Amino Acids

These substrates were determined both in arterial (radial artery) and venous blood of the unaffected arm. Concentrations of free amino acids in the plasma were measured using an AminoQuant II amino acid analyser, based on the HP 1090 HPLC system, with fully automated pre-column derivatization, using both orto-phthalaldehyde and 9-fluorenyl-methyl-chloroformate reaction chemistries according to the manufacturer's protocol. The results were obtained by injecting 1 µl of the derivatized mixture and measuring absorbance simultaneously at 338 and 262 nm. Plasma concentrations were expressed as µmol/l. Amino acid measurements were carried out as a comparison in eight healthy subjects matched for age (71±4.5 years), sex distribution (6 M/2 F), body mass index (22.3±3.5 kg/m$^2$).

Calculations a) Muscle protein metabolism. As described elsewhere (Aquilani et al., 2012), muscle protein over-degradation was estimated by the muscle release of the essential amino acid phenylalanine (phenyl-), whereas muscle protein synthesis was determined by muscle phenyl- uptake. Given that phenyl- is neither synthesized nor degraded in muscle tissue, any changes in the muscle uptake/release would reflect the total protein balance (Liu and Barret, 2002).

A negative phenyl- A-V (=release) signified an imbalanced protein metabolism with an excess of protein degradation over protein synthesis, whereas a positive phenyl- A-V (=uptake) indicated a predominance of protein synthesis. A phenyl- A-V of zero (no uptake/no release) indicated a balanced muscle protein metabolism.

b) A-V differences of the other amino acids, total amino acids (TAAs), total essential amino acids (EAAs: valine, isoleucine, leucine, threonine, phenyl-, tryptophan, methionine, lysine), branched-chain amino acids (BCAAs: valine, isoleucine, leucine).

2) Biomarkers of Body Inflammatory Status i) Serum levels of interleukine-6 (IL-6; normal value<7 pg/ml), were determined in duplicate, using a high-sensitivity commercial sandwich enzyme-linked immunosorbent assay (ELISA) kit from Mabtech (Agilent Technologies GmbH, Boblingen, Germany);

ii) C-reactive protein (CRP; normal value<0.3 mg/dl), was determined with an immune-turbidimetric method;

iii) acute-phase reactant proteins (haptoglobin, normal values 30-200 mg/dl; α-1 globulin system, normal value 0.21-0.35 g/dl; non-reactant proteins (albumin, normal values 4.02-4.76 g/dl; prealbumin, normal values 18-30 mg/dl and transferrin, normal values 202-364 mg/dl).

3) Plasma Lactate Concentrations

These were measured with enzymatic tests following procedures recommended by the manufacturer (Siemens Diagnostic, Germany). The normal value is 0.6-2.2 mmol/l.

4) As Part of Routine Assessment, Patients Had the Following Variables Measured:

i) anthropometric characteristics: body weight (BW, kg), found using a mechanical weight lifter; height (m), calculated from knee height (Chumlea et al., 1985). Body mass index (BMI) was calculated as $kg/m^2$. Patients (or their caregivers) were asked for their pre-acute BW. Loss of actual BW in relation to habitual (pre-acute) BW>5% i.e. actual/habitual BW<95% was considered an index of significant under-nutrition;

ii) bio-humoral measurements: routine variables, including serum protein electrophoresis.

5) Functional Status

This was evaluated using Functional Independence Measure (FIM) (Keith et al., 1987). This test is routinely used by the centre's neuro-rehabilitative physician. The FIM is a 18-item scale that measures patient independence in feeding, grooming, dressing, toileting, mobility, cognition. A score of 126 indicates complete functional independence.

6) Dysphagia

Identification of dysphagia was carried out clinically for the entire population. In case of positive or uncertain diagnosis, the patients underwent a video fluoroscopy examination. The severity of the dysphagia was evaluated using the Dysphagia Outcome and Severity Scale (DOSS), a 7-point scale developed to systematically rate the functional severity of dysphagia (O'Neil et al., 1999). The score range was 1-7, where level 1 denotes severe dysphagia, level 2 moderately-severe dysphagia, level 3 moderate-dysphagia, level 4 mild-to-moderate dysphagia, level 5 mild-dysphagia, level 6 within functional limit/modified independence and level 7 normal under all situations.

7) Nutritional Intake

For self-feeding patients (n=8) on a modified diet, a 3-day alimentary diary was kept by the rehabilitation nurses, who had been previously trained ad hoc. The nurses recorded the type and weight of cooked or uncooked food selected by patients from the hospital's catering menu on a diet sheet for 3 days both before and after the patients' meals. The amount of food actually ingested was converted to its raw equivalent when necessary, using appropriate tables (Carnevale et al., 1989). Nutritional analysis, carried out using a computer program designed by this group (Aquilani et al., 1999), was used to calculate actual ingested calories and macro-/micro-nutrients. The nutritional intake from pharmaceutical formula of the patients with PEG (n=30) were calculated from nutritional composition reported in the formula label.

8) Rehabilitation Therapy

All patients received rehabilitative treatment adapted to each individual patients. Briefly, rehabilitation consisted of therapeutic exercise with a personal physiotherapist for 60 minutes, five days a week. The exercise included passive, active and active-assistive range-of-motion exercise coordination, facilitation techniques of the contro-lateral limbs, trunk exercise, active exercises of the unaffected limbs and ambulation with assistive devices or support. The number or repetition in exercise and walking distance were increased as the physical performance of the patients progressed. Speech therapy, occupational therapy (activities of daily living, vocational, perceptual and functional activity training), recreational activity were also performed depending on individual needs.

For dysphagia rehabilitation, attempts were made to provide patients with a DOSS levels ≥3 with a modified diet as well as teaching safe swallowing postural changes. For the diet, pureed, homogeneous and cohesive foods were initially used with a gradual progression to food with nearly normal texture for individuals whose swallowing dysfunction progressively improved.

Postural changes during meals usually consisted of patients adapting techniques, which reduced the risk of aspiration. These included, for example, head rotation to the affected side, tilting of the head to the stronger side, chin tuck, chin up movements.

For patients with DOSS<3 attempts were made for oral transition after videofluoroscopic and/or after speech pathologists' assessments. If patients could safely eat at least two-third of their prescribed calories (1500 kcal/d), then tube feeding was discontinued.

Patient randomization. After completing all these procedures, patients were assigned to treatment according to a randomized allocation procedure (FIG. 1). A randomization list was generated using SAS statistical software (SAS Institute, Cary, N.C.). A and B were the identifiers of the blinded treatment. The list was made available both to the physician and to hospital pharmacists. The physician sequentially allocated patients to treatment A or B according to a randomization list. The first investigator, who interpreted all results was blinded to the patients' allocation. The experimental group (EAA group) received the composition herein disclosed that provided 8 g of essential aminoacids/day (Table 2; 4 g in the morning+4 g in the afternoon diluted in about half a glass of water until patient discharge).

TABLE 2

| Ingredients | mg |
|---|---|
| Total amino acids including the following | 4000 (in total) |
| L-Leucine (131.17)* | 1250.00 |
| L-Isoleucine (131.17)* | 625.00 |
| L-Valine (117.15)* | 625.00 |
| L-Lysine (146.19)* | 650.00 |
| L-Threonine (119.12)* | 350.00 |
| L-Histidine (155.16)* | 150.00 |
| L-Phenylalanine (165.19)* | 100.00 |
| L-Methionine (149.21)* | 50.00 |
| L-Tryptophan (204.23)* | 20.00 |
| L-Tyrosine (181.19)* | 30.00 |
| L-Cystine (240.30)* | 150.00 |
| Other ingredients | |
| Vitamin B6 | 0.15 |
| Vitamin B1 | 0.15 |
| Carbohydrates - Maltodextrins | 5454.10 |
| Xanthan gum | 750.00 |
| Methylhydroxypropylcellulose | 500.00 |
| Banana flavour | 200.00 |
| Sodium citrate tribasic dehydrate | 150.00 |
| Aspartame powder | 30.00 |
| Acesulfame potassium | 17.50 |
| Energetic value | |
| Kcal | 24.80 |
| Kj | 102.20 |

*Molecular weight from "Amino Acid, Nucleic Acids & Related Compounds - Specification/General Tests", 8th Edition, Kyowa Hakko Kogyo Co., Ltd.

As observable from Table 2, the weight ratios between leucine, isoleucine and valine are preferably equivalent to 2:1:1. Table 1 also show that the single amounts of histidine, phenylalanine, methionine and tryptophan are preferably decreasing (i.e. the amount of histidine is greater than phenylalanine, which is greater than methionine, which is greater than tryptophan) and the amount (weight in grams or moles) of cystine is preferably greater than tyrosine.

The composition shown in Table 2 is prepared first by loading in a four-way mixer L-fenilalanine, L-Tyrosine, L-Tryptophan, Vitamin B1 and Vitamin B6 together with L-Lysine, in order to obtain a pre-mixture. The % composition of the pre-mixture is represented in Table 3 below.

TABLE 3

| Ingredients | % |
|---|---|
| Maltodextrins | 83.296 |
| L-Phenylalanine | 8.333 |
| L-Methionine | 4.167 |
| L-Tyrosine | 2.500 |
| L-Tryptophan | 1.667 |
| Vitamin B1 | 0.019 |
| Vitamin B6 | 0.018 |

The ingredients are mixed for a period of 10 minutes in order to obtain a homogeneous pre-mixture.

The remainder of the ingredients listed in Table 1 are loaded in the four-way mixer and mixed for a period of 20 minutes to obtain a homogeneous final composition.

Table 4 lists the characteristics of the composition obtained as above described:

TABLE 4

| | |
|---|---|
| Aspect | Granular mixture of powders |
| Colour | White |
| Smell | Smell of banana |
| Taste | Sour taste |
| Granulometry | <0.8 mm 95% min. |
| Pour Bulk Density (g/l) | 430 (±20%) |
| Aspect of the suspension in water (60 ml) | Yellowish, very viscous. Left to rest for 5 minutes assumes semi-solid consistency |
| Dispersion time in water (60 ml) | <180 seconds |

The composition object of the present description is added and dispersed in a liquid, preferably water. The amount of liquid to add to the composition herein disclosed depends, for example, on the consistency that is necessary to obtain. This parameter is evaluated and determined by a person skilled in the field also taking into account the degree of dysphagia of the patient.

The placebo group (Plac) was given a similar isocaloric product containing maltodextrin instead of the active agent comprising the amino acids. Rehabilitation nurses assisted each patient with their oral diet during placebo or the composition herein disclosed (EAAs) intake to be sure of the patients' compliance.

The nurses were blinded to the type of supplementation (Plac or EAAs), the packets containing the products were identical but numbered as 1 or 2. The contents were known only to the physician and pharmacists (1=placebo; 2=EAAs). The product content in packets 1 and 2 had a similar colour and taste. For patients receiving enteral nutrition (EN), the aqueous solution of the composition herein disclosed was supplied through the feeding tube (percutaneous endoscopy gastrostomy). The study lasted 38±4 days from the randomization procedure Amino acids, inflammation markers as well as anthropometric and functional status measures were all repeated at the patients' discharge from rehabilitation (42±4 days from admission). The study was approved by the Ethical-Technical Scientific Committee of the Institute. Written informed consent was obtained from participants or, whenever applicable, from their care-givers, after the nature of the study had been fully explained.

Statistical Analysis. Descriptive statistics were carried out for all recorded variables, reporting means and standard deviations for quantitative variables and distribution frequencies for qualitative variables. Chi-squared test was used for categorical variables. Repeated measurement analysis of variance was used to assess any trend differences over time between patients on EAAs or Plac. Baseline differences between groups (EAAs and Plac) and differences in amino acid profiles between the entire stroke population at the admission to rehabilitation and healthy controls were tested by means of unpaired student t-test. Statistical significance was set at $p<0.05$.

Results

All patients who entered this study were randomized to receive the composition herein disclosed (EAAs) or placebo (Plac) (FIG. 1).

1) Unaffected Arm Muscle Protein Turnover.

Table 5 shows arterial amino acid concentrations and muscle amino acid artero-venous differences (A-V) encountered for both stroke patients at admission to rehabilitation and healthy subjects.

TABLE 5

| Amino acid profiles (µmol/l) | Healthy subjects (n = 8) | Stroke (n = 38) | p value |
|---|---|---|---|
| Aspartate | | | |
| A | 98.1 ± 40.6 | 16.6 ± 6.7 | p = 0.001 |
| A-V | −0.3 ± 14.3 | 0.55 ± 4.7 | p = 0.9 |
| Glutamate | | | |
| A | 198.7 ± 10.6 | 195.5 ± 137.3 | p = 0.9 |
| A-V | −7.5 ± 21 | −6.5 ± 55.9 | p = 0.8 |
| Histidine | | | |
| A | 58 ± 5.1 | 55.5 ± 10.3 | p = 0.7 |
| A-V | −0.4 ± 5 | −6.1 ± 8.7 | p = 0.3 |
| Asparagine | | | |
| A | 61 ± 1.1 | 35.5 ± 10.5 | p < 0.001 |
| A-V | 4.9 ± 5.5 | −4.3 ± 6.6 | p = 0.002 |
| Serine | | | |
| A | 88.4 ± 4.3 | 108 ± 35.7 | p = 0.025 |
| A-V | −2.4 ± 6.4 | 1.5 ± 24.6 | p = 0.6 |
| Glutamine | | | |
| A | 464.8 ± 14 | 323.5 ± 184.2 | p = 0.003 |
| A-V | −2.4 ± 23 | −18.2 ± 67.2 | p = 0.2 |
| Arginine | | | |
| A | 59.3 ± 7.6 | 89.1 ± 69.42 | p = 0.6 |
| A-V | 7.3 ± 19.5 | 18 ± 62.4 | p = 0.3 |
| Citrulline | | | |
| A | 24.2 ± 3.8 | 30.3 ± 14 | p = 0.7 |
| A-V | −0.9 ± 5.6 | 1.2 ± 7.3 | p = 0.5 |
| Glycine | | | |
| A | 268.3 ± 12 | 239.3 ± 60.9 | p = 0.8 |
| A-V | 9.9 ± 29.9 | −19.4 ± 41.8 | p = 0.2 |
| *Threonine | | | |
| A | 106.6 ± 11 | 120.4 ± 41.5 | P = 0.8 |
| A-V | −0.8 ± 14.8 | −12.2 ± 10.5 | p = 0.029 |
| Alanine | | | |
| A | 312.6 ± 15.7 | 259.3 ± 84 | p = 0.012 |
| A-V | −15 ± 20.5 | −68.5 ± 40.4 | p = 0.002 |
| Taurine | | | |
| A | 125.8 ± 9.7 | 55.6 ± 23.1 | p < 0.001 |
| A-V | 8.1 ± 12.9 | −34 ± 23 | p < 0.001 |
| Tyrosine | | | |
| A | 56.3 ± 6.1 | 57.4 ± 21.3 | p = 0.9 |
| A-V | 4.5 ± 9.1 | −2.75 ± 11 | p = 0.4 |

TABLE 5-continued

| Amino acid profiles (µmol/l) | Healthy subjects (n = 8) | Stroke (n = 38) | p value |
|---|---|---|---|
| *°Valine | | | |
| A | 155 ± 12.5 | 229.4 ± 47.7 | p = 0.005 |
| A-V | 4.4 ± 18.9 | −15.5 ± 16.6 | p = 0.064 |
| *Methionine | | | |
| A | 10.75 ± 1.7 | 35.1 ± 6.6 | p < 0.001 |
| A-V | 0.7 ± 1.9 | −0.3 ± 4.9 | p = 0.5 |
| *Tryptophan | | | |
| A | 51.1 ± 4.6 | 33.9 ± 7.8 | p < 0.001 |
| A-V | −0.5 ± 7.6 | −3.7 ± 4.1 | p = 0.5 |
| *Phenylalanine | | | |
| A | 46.3 ± 5.7 | 67.4 ± 26.6 | p = 0.037 |
| A-V | 0.3 ± 6.6 | −6.9 ± 8.1 | p < 0.03 |
| *°Isoleucine | | | |
| A | 45.8 ± 5 | 76 ± 17.7 | p < 0.001 |
| A-V | 1.1 ± 5.7 | −6.4 ± 8.5 | p = 0.5 |
| *°Leucine | | | |
| A | 78.13 ± 6.35 | 135.6 ± 36.4 | p < 0.001 |
| A-V | 0.38 ± 7.2 | −18.8 ± 33.3 | p = 0.02 |
| Ornithine | | | |
| A | 56.4 ± 6.4 | 60.9 ± 20.9 | p = 0.8 |
| A-V | 1 ± 10.5 | −10.1 ± 8.7 | p = 0.01 |
| *Lysine | | | |
| A | 115.8 ± 11 | 201.4 ± 71.6 | p < 0.001 |
| A-V | −1.3 ± 16.7 | −12.6 ± 53 | p = 0.4 |
| Total-amino acids | | | |
| A | 24.81 ± 60.5 | 2425.7 ± 601 | p = 0.2 |
| A-V | 13.24 ± 78.1 | −225 ± 267.6 | p = 0.6 |
| *EAAs | | | |
| A | 609.4 ± 18.9 | 899.2 ± 194.1 | p = 0.5 |
| A-V | 4.3 ± 21.2 | −76.4 ± 167 | p = 0.3 |
| °BCAAs | | | |
| A | 279 ± 13.2 | 441 ± 88.4 | p = 0.2 |
| A-V | 5.9 ± 25.7 | −40.7 ± 59 | p = 0.09 |

Data are expressed as mean ± standard deviation (SD).
Statistical analysis: Unpaired t-test.
*Essential Amino Acids (EAAs);
°Branched Chain Amino Acids (BCAAs)

The results showed that muscle protein metabolism of the unaffected side was prevalently in a hypercatabolic state (MH) due to excess of protein catabolism over protein synthesis indicated by muscle release of phenyl-. This was significantly different (p<0.03) from healthy subjects whose muscle protein metabolism was in equilibrium. In addition to phenyl-, patients released significant amounts of asparagine, threonine, leucine, alanine and taurine.

Regarding arterial amino acid concentrations, stroke patients had higher levels of serine, methionine, phenyl-, isoleucine, leucine, lysine but lower concentrations of aspartic acid, asparagine, glutamine, alanine, taurine, tryptophan. A sub-analisys of patients divided into type of cerebrovascular accident (ischaemic or haemorrhagic), revealed similar results.

Table 6 shows the amino acid profiles of the two patient sub-groups randomized to receive the composition herein disclosed (Table 2, EAAs) or Plac, both at admission to and discharge from rehabilitation. At admission, the two sub-groups had no significant difference in the MH rate (=phenyl- release), in the other amino acid and total amino acid (TAA) A-V differences. Arterial concentrations of individual amino acids, of TAAs and of EAAs were similar for both EAA and Plac.

At discharge, patients who assumed the composition herein disclosed (EAA) but not Plac patients normalized their protein metabolism in the unaffected arm. Indeed, the release of phenyl- shifted to muscle uptake in treated patients but remained virtually unchanged in Plac patients. This difference in the time course of (A-V) phenyl- was significant (interaction, D=0.02).

TABLE 6

| Amino acid profiles (µmol/l) | Admission | | | Discharge | | | ^Trend over time (p level) interaction |
|---|---|---|---|---|---|---|---|
| | Placebo (n = 19) | EAAs (n = 19) | §p value | Placebo (n = 19) | EAAs (n = 19) | | |
| Aspartate | | | | | | | |
| A | 16.27 ± 7.3 | 17.11 ± 6.4 | p = 0.1 | 17.3 ± 6 | 17.5 ± 10.6 | | p = 0.1 |
| A-V | 1 ± 5.2 | 0.01 ± 4.3 | p = 0.2 | −2 ± 4.3 | 2.8 ± 5.5 | | p = 0.04 |
| Glutamate | | | | | | | |
| A | 207 ± 153.5 | 181.6 ± 122 | p = 0.2 | 171.1 ± 102.3 | 150 ± 102.8 | | p = 0.3 |
| A-V | −12.7 ± 71.3 | 1.1 ± 31 | p = 0.5 | −14.7 ± 35 | 4.7 ± 37.4 | | p = 0.8 |
| Histidine | | | | | | | |
| A | 59.36 ± 10.8 | 50.9 ± 8 | p = 0.1 | 59.2 ± 11.8 | 68.9 ± 13.6 | | p = 0.7 |
| A-V | −4.6 ± 9.3 | −8 ± 8 | p = 0.4 | −7.7 ± 4.8 | −1.4 ± 6.2 | | p = 0.02 |
| Asparagine | | | | | | | |
| A | 39 ± 7.7 | 38 ± 13.5 | p = 0.1 | 35.4 ± 5.4 | 43.1 ± 10.4 | | p = 0.05 |
| A-V | −2.8 ± 5.4 | −6 ± 7.8 | p = 0.7 | −5.2 ± 3.5 | −1.1 ± 4.2 | | p = 0.03 |
| Serine | | | | | | | |
| A | 115 ± 42.9 | 99.3 ± 24.1 | p = 0.1 | 107.8 ± 30.2 | 119 ± 40.6 | | p = 0.9 |
| A-V | 0.9 ± 25 | 2.22 ± 25.5 | p = 0.6 | −1.3 ± 19.6 | 15.2 ± 31.1 | | p = 0.5 |

TABLE 6-continued

| Amino acid profiles (µmol/l) | Admission | | | Discharge | | Trend over time (p level) interaction |
|---|---|---|---|---|---|---|
| | Placebo (n = 19) | EAAs (n = 19) | §p value | Placebo (n = 19) | EAAs (n = 19) | |
| Glutamine | | | | | | |
| A | 323.3 ± 192.8 | 323.8 ± 184.8 | p = 0.4 | 378 ± 131.6 | 463.6 ± 99 | p = 0.4 |
| A-V | 6.6 ± 75.5 | −48.4 ± 41.7 | p = 0.07 | −10.8 ± 69.6 | −22.6 ± 31.6 | p = 0.07 |
| 3methylhistidine | | | | | | |
| A | 3 ± 1.2 | 2.2 ± 1 | p = 0.2 | 2.4 ± 1.4 | 2.4 ± 1.1 | p = 0.2 |
| A-V | 0.3 ± 1.1 | −0.1 ± 0.1 | p = 0.2 | −0.2 ± 1.1 | −0.03 ± 1.1 | p = 0.1 |
| Arginine | | | | | | |
| A | 103.7 ± 86.2 | 71.2 ± 38.8 | p = 0.3 | 98.4 ± 57.1 | 104.9 ± 65.2 | p = 0.08 |
| A-V | 30.6 ± 81.6 | 2.7 ± 20.9 | p = 0.5 | 10.8 ± 61.7 | 40.4 ± 62.1 | p = 0.07 |
| Citrulline | | | | | | |
| A | 33.7 ± 12.2 | 26.1 ± 15.7 | p = 0.2 | 35.7 ± 13.7 | 35.6 ± 21.1 | p = 0.4 |
| A-V | 2.3 ± 9.6 | −0.2 ± 3.2 | p = 0.5 | −3 ± 5.6 | 0.3 ± 1.3 | p = 0.09 |
| Glycine | | | | | | |
| A p= | 243.6 ± 71.7 | 233.9 ± 48.1 | p = 0.2 | 240.9 ± 40.4 | 308.1 ± 9 | p = 0.08 |
| A-V | −7.4 ± 48.9 | −34 ± 26.8 | p = 0.8 | −38.1 ± 21.3 | −9.3 ± 24.5 | p = 0.01 |
| *Threonine | | | | | | |
| A | 113.3 ± 19.5 | 129 ± 58.9 | p = 0.2 | 131.8 ± 52.6 | 157.7 ± 54.6 | p = 0.5 |
| A-V | −11.5 ± 8.6 | −13 ± 12.9 | p = 0.2 | −10.5 ± 16.2 | 2.4 ± 15.5 | p = 0.09 |
| Alanine | | | | | | |
| A | 242.3 ± 78.2 | 280.1 ± 90.8 | p = 0.1 | 274.7 ± 76.1 | 365.5 ± 61.6 | p = 0.6 |
| A-V | −70.5 ± 27 | −66 ± 54.4 | p = 0.2 | −58.9 ± 68.7 | −33 ± 50.2 | p = 0.08 |
| Taurine | | | | | | |
| A | 61.8 ± 20.7 | 4 ± 24.8 | p = 0.08 | 43.7 ± 5.9 | 37.3 ± 16.2 | p = 0.09 |
| A-V | −33 ± 29.5 | −35.3 ± 13.2 | p = 0.3 | −52 ± 21.4 | −27.1 ± 13.6 | p = 0.006 |
| Tyrosine | | | | | | |
| A | 56.5 ± 10.9 | 58.4 ± 30.4 | p = 0.1 | 49.2 ± 14.8 | 62.1 ± 27.2 | p = 0.8 |
| A-V | −4.5 ± 5.5 | −0.7 ± 15.6 | p = 0.4 | −4.8 ± 2.7 | 1.9 ± 7.8 | p = 0.03 |
| *°Valine | | | | | | |
| A | 265.7 ± 39.8 | 202.3 ± 33.7 | p = 0.4 | 198.7 ± 49.1 | 248.5 ± 31.8 | p = 0.6 |
| A-V | −12.5 ± 20.5 | −17 ± 17.6 | p = 0.07 | −18 ± 12.7 | 0.05 ± 21.2 | p = 0.7 |
| *Methionine | | | | | | |
| A | 36 ± 8.7 | 34.5 ± 5.9 | p = 0.2 | 27.7 ± 16.8 | 26 ± 2.8 | p = 0.5 |
| A-V | 0.5 ± 0.7 | −0.8 ± 6.3 | p = 0.3 | 3.5 ± 14.8 | −2 ± 2.8 | p = 0.7 |
| *Tryptophan | | | | | | |
| A | 35 ± 8.1 | 32.4 ± 7.7 | p = 0.1 | 33.1 ± 8.4 | 36.1 ± 9.1 | p = 0.8 |
| A-V | −3.1 ± 4.6 | −4.3 ± 3.7 | p = 0.2 | −3.3 ± 3.3 | −0.4 ± 6.1 | p = 0.3 |
| *Phenylalanine | | | | | | |
| A | 69.7 ± 21.9 | 64.4 ± 32.5 | p = 0.1 | 51.4 ± 11.1 | 56.7 ± 11.8 | p = 0.5 |
| A-V | −6.9 ± 7.6 | −6.8 ± 9.1 | p = 0.1 | −6 ± 4.4 | 0.9 ± 7.6 | p = 0.02 |
| *°Isoleucine | | | | | | |
| A | 81.9 ± 12.2 | 68.8 ± 21.2 | p = 0.3 | 85.4 ± 65.6 | 111.5 ± 73.1 | p = 0.09 |
| A-V | −6.4 ± 22 | −6.3 ± 14.5 | p = 0.1 | 6 ± 28.3 | 11.6 ± 17.6 | p = 0.5 |
| *°Leucine | | | | | | |
| A | 148.6 ± 30.8 | 119.6 ± 38 | p = 0.07 | 149.6 ± 134.2 | 191.7 ± 119.1 | p = 0.4 |
| A-V | −13.8 ± 28 | −24.2 ± 39.2 | p = 0.5 | 7.7 ± 16.4 | 11.7 ± 26.4 | p = 0.8 |
| Ornithine | | | | | | |
| A | 63.7 ± 12.6 | 58.1 ± 27.4 | p = 0.5 | 56 ± 13.9 | 57.3 ± 22.8 | p = 0.8 |
| A-V | −13.4 ± 9.3 | −6.7 ± 7 | p = 0.09 | −17.6 ± 17.6 | −2.1 ± 21 | p = 0.08 |
| *Lysine | | | | | | |
| A | 205.3 ± 77 | 196.7 ± 68.6 | p = 0.7 | 209.6 ± 95.6 | 248.2 ± 124 | p = 0.8 |
| A-V | −8.3 ± 67.2 | −17.8 ± 31.3 | p = 0.6 | −1.9 ± 64.3 | 58.3 ± 122.1 | p = 0.7 |
| Total-amino acids | | | | | | |
| A | 2523.7 ± 331.8 | 2292.4 ± 472.7 | p = 0.3 | 2457.1 ± 826.8 | 2747 ± 465.9 | p = 0.02 |
| A-V | −169.2 ± 25.6 | −289.6 ± 18 | p = 0.5 | −63.8 ± 25.7 | 51.2 ± 23.5 | p = 0.05 |

TABLE 6-continued

| Amino acid profiles (µmol/l) | Admission | | | Discharge | | Trend over time (p level) interaction |
| --- | --- | --- | --- | --- | --- | --- |
| | Placebo (n = 19) | EAAs (n = 19) | §p value | Placebo (n = 19) | EAAs (n = 19) | |
| *EAAs | | | | | | |
| A | 956 ± 103 | 848 ± 242 | p = 0.5 | 887.3 ± 254 | 1076.4 ± 295 | p = 0.05 |
| A-V | −62 ± 20 | −90.2 ± 16.9 | p = 0.3 | −22.5 ± 20 | 82.6 ± 27.4 | p = 0.01 |
| °BCAAs | | | | | | |
| A | 493.6 ± 57.3 | 391 ± 84.5 | p = 0.5 | 433.7 ± 213.9 | 552 ± 225.9 | p = 0.09 |
| A-V | −32.7 ± 23.5 | −47.5 ± 23.8 | p = 0.6 | −4.3 ± 19 | 23.35 ± 21.7 | p = 0.05 |

Data are expressed as mean ± standard deviation (SD).
Statistical analysis: §unpaired t-test; ^repeated measures analysis of variance.
Trend over time: interaction differences in trends between groups.
*Essential amino acids (EAAs);
°branched chain amino acids (BCAAs).

Figure 2:
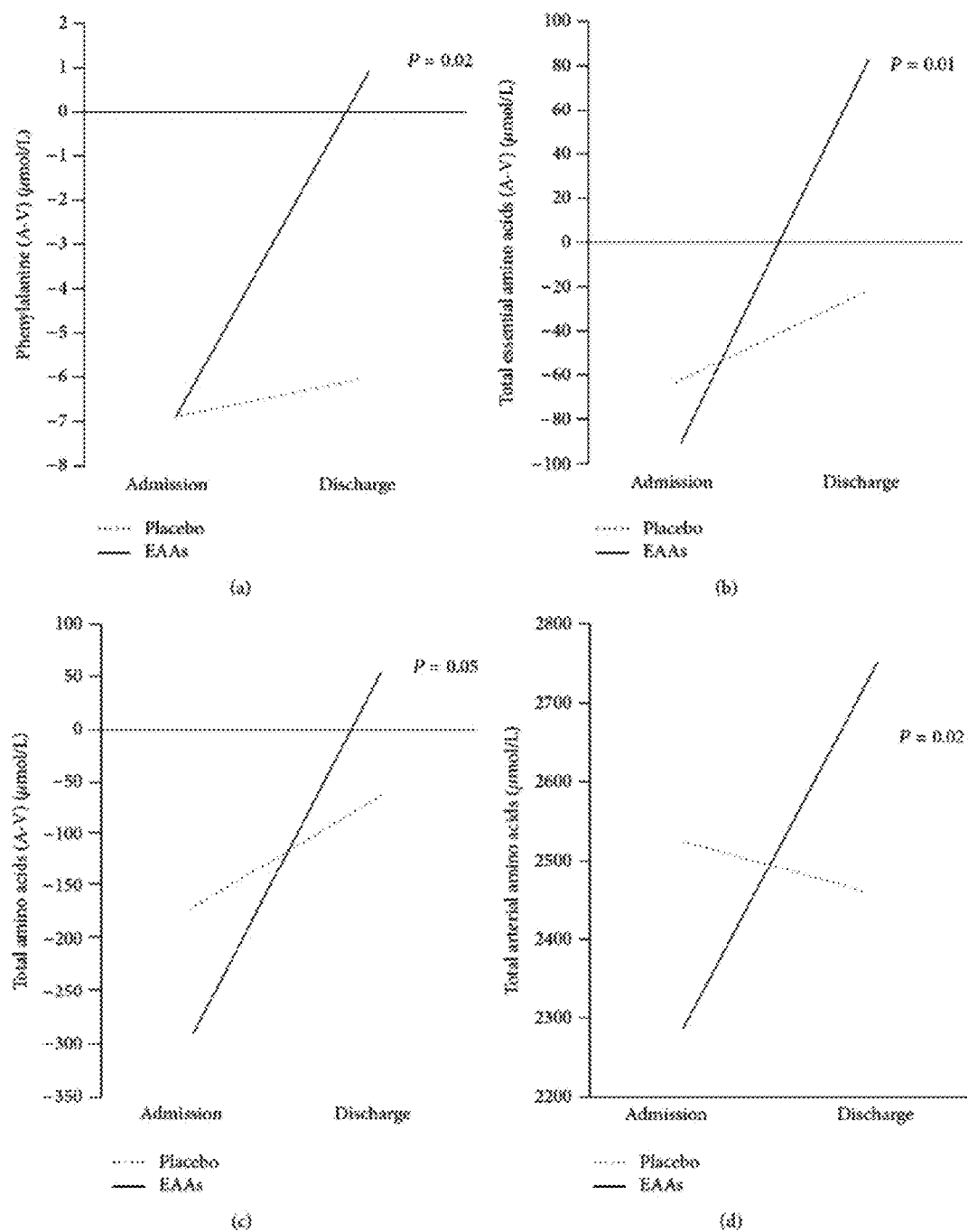
FIG. 2 represents the time courses of phenyl-, total essential amino acid, total amino acid (A-V) differences, and total arterial amino acid levels of stroke population. The point 0 indicates no uptake/no release.

FIG. 2 shows the discrepancy between the two sub-groups also entailed arterial TAAs (p=0.02), TAAs (A-V) (p=0.05), EAAs (A-V) (p=0.01), BCAAs (A-V) (p=0.05), not shown in the figure).

Indeed, of all measured amino acids, 49% of them were taken up by EAA subjects (subject who assumed the composition herein disclosed), while only 23.2% by Plac ones (p<0.001). The time courses of A-V differences between the two groups were also different for aspartic acid, histidine, asparagine, glycine, taurine, tyrosine, released more in Plac than in the EAA groups. In the latter patients, aspartic acid was not released/not taken up.

2) Other Study Variables.

Table 7 shows demographic-, anthropometric-, neurofunctional-, biohumoral- characteristics as well as nutritional intakes of stroke patients both as an entire group and of the two sub-groups after randomization both at admission and discharge. At admission all subjects were malnourished due to post-event weight loss compared to their habitual BW (−9.7%). The patients' were inflamed as shown by high serum levels of IL-6 and CRP with consequent reduced concentrations of negative reactants of acute phase response (albumin, prealbumin, transferrin) and increased concentrations of positive ones (haptoglobin, ai globuline).

TABLE 7

| Variables | nv | All patients (n = 38) | | Placebo (n = 19) | | EAAs (n = 19) | | Trend over time (p level) interact. |
| --- | --- | --- | --- | --- | --- | --- | --- | --- |
| | | admission | discharge | admission | discharge | admission | discharge | |
| Demographic | | | | | | | | |
| Male/Female | — | 25/13 | — | 13/6 | — | 12/7 | — | — |
| Age (years) | — | 69.7 ± 11.4 | — | 71.3 ± 10 | — | 68 ± 13.2 | — | — |
| Anthropometric | | | | | | | | |
| Actual body weight (kg) | — | 59.8 ± 10.2 | 57.7 ± 9.8 | 57.6 ± 7.1 | 55.9 ± 7.5 | 62.2 ± 12.7 | 59.7 ± 12 | p = 0.6 |
| Actual/habitual body weight (%) | — | 90.4 ± 7.4 | 87.5 ± 9.5 | 90.5 ± 7.2 | 87.8 ± 9.3 | 90.3 ± 8 | 87.1 ± 10.3 | p = 0.8 |
| BMI (kg/m$^2$) | — | 21.6 ± 3 | 20.88 ± 3.14 | 21.3 ± 2.6 | 20.7 ± 2.9 | 22 ± 3.5 | 21.1 ± 3.5 | p = 0.8 |
| Blood | | | | | | | | |
| ESR 1$^{st}$ hr (mm) | 2-20 | 35.8 ± 11.7 | 33.2 ± 18.1 | 31.2 ± 6.8 | 27.6 ± 16 | 43.3 ± 15.8 | 37.2 ± 19.7 | p = 0.7 |
| Haemoglobin (g/dl) | F > 12; M > 13 | 12.2 ± 1.6 | 12.1 ± 1.2 | 12.6 ± 1.8 | 12.3 ± 1.3 | 11.7 ± 1 | 12 ± 1.1 | p = 0.07 |
| Blood urea (mg/dl) | 20-40 | 42.7 ± 19.7 | 37.5 ± 19 | 48.70 ± 15 | 37.6 ± 7.6 | 32.7 ± 23.7 | 37.3 ± 26 | p = 0.9 |
| Serum creatinine (mg/dl) | 0.7-1.2 | 1 ± 0.3 | 1 ± 0.3 | 1.1 ± 0.4 | 1.1 ± 0.3 | 0.8 ± 0.2 | 0.9 ± 0.3 | p = 0.5 |
| Plasma glucose (mg/dl) | 80-110 | 115.1 ± 23.6 | 106.9 ± 11.6 | 122.5 ± 25.8 | 104.8 ± 14.1 | 100.3 ± 8.5 | 109.7 ± 9.3 | p = 0.07 |
| Interleukin-6 (pg/ml) | <7 | 15.9 ± 14.9 | 6.7 ± 9.86 | 11.7 ± 9 | 8.5 ± 13.5 | 19.6 ± 18.5 | 4.6 ± 2.3 | p = 0.5 |
| Serum C-reactive Protein (CRP) (mg/dl) | <0.3 | 1.9 ± 1.9 | 1.4 ± 2.5 | 1.7 ± 1.3 | 1.6 ± 2.8 | 2.2 ± 2.5 | 1.2 ± 2.3 | p = 0.6 |
| Fibrinogen (mg/(dl) | 230-550 | 452.4 ± 75.8 | 400.9 ± 87.9 | 465.1 ± 87.3 | 387.2 ± 68.2 | 438 ± 63.1 | 412.7 ± 106 | p = 0.8 |
| Serum haptoglobin (mg/dl) | 30-200 | 293.6 ± 93 | 211 ± 75 | 313 ± 94 | 245 ± 74 | 272 ± 92 | 169 ± 56 | p = 0.7 |
| Serum α1 globulin (mg/dl) | 210-350 | 504 ± 74 | 436 ± 89 | 506 ± 80 | 467 ± 92 | 472 ± 79 | 382 ± 85 | p = 0.8 |
| Serum albumin (g/dl) | 4.02-4.76 | 2.9 ± 0.5 | 3.2 ± 0.5 | 3 ± 0.5 | 3.1 ± 0.5 | 2.7 ± 0.6 | 3.3 ± 0.5 | p = 0.03 |
| Serum prealbumin (mg/dl) | 18-30 | 18.8 ± 5.7 | 20.9 ± 7.1 | 19.4 ± 6.5 | 19 ± 5.9 | 18.1 ± 4.9 | 22.9 ± 8.1 | p = 0.7 |
| Serum transferrin (mg/dl) | 202-364 | 183.1 ± 28.3 | 193.8 ± 35.1 | 186.1 ± 33.2 | 195.4 ± 39.6 | 179.3 ± 22.3 | 192 ± 31.8 | p = 0.5 |
| Plasma lactate (mmol/l) | 0.6-2.2 | 1.6 ± 0.5 | 2 ± 0.6 | 1.4 ± 0.4 | 2 ± 0.6 | 1.8 ± 0.5 | 2 ± 0.5 | p = 0.3 |
| Neurofunction | | | | | | | | |
| FIM score | 125 | 29.4 ± 18.5 | 54 ± 31.2 | 31.1 ± 16 | 60 ± 36.8 | 27.6 ± 21.7 | 47.4 ± 23.9 | p = 0.5 |
| DOSS score | 1-7 | 2.1 ± 1.3 | 3.3 ± 1.7 | 2.5 ± 1.3 | 3.9 ± 1.8 | 1.6 ± 1.3 | 2.6 ± 1.5 | p = 0.7 |
| Nutrition | | | | | | | | |

TABLE 7-continued

| Variables | nv | All patients (n = 38) | | Placebo (n = 19) | | EAAs (n = 19) | | Trend over time (p level) interact. |
|---|---|---|---|---|---|---|---|---|
| | | admission | discharge | admission | discharge | admission | discharge | |
| (PEG or oral intake) | | | | | | | | |
| Energy | | | | | | | | — |
| (kcal/d) | — | 1293.6 ± 155 | same | 1362 ± 143 | same | 1293 ± 155 | same | |
| (kcal/kg) | ≥25 | 22.4 ± 2.7 | | 23.6 ± 2.5 | | 20.7 ± 2.9 | | |
| Protein | | | | | | | | — |
| (g/d) | — | 54.1 ± 9.6 | same | 58.7 ± 10.2 | same | 54.2 ± 9.6 | same | |
| (g/kg) | ≥1.1 | 0.94 ± 0.17 | | 1.02 ± 0.17 | | 0.87 ± 0.19 | 1.02 ± 0.20* | |
| Carbohydrates | | | | | | | | — |
| (g/d) | — | 146.2 ± 32 | same | 164.3 ± 30.1 | same | 146.2 ± 32 | same | |
| (g/kg) | 2.5-4 | 2.5 ± 0.5 | | 2.85 ± 0.2 | | 2.35 ± 0.9 | | |
| Lipids | | | | | | | | — |
| (g/d) | — | 56.9 ± 11 | same | 55.3 ± 5.5 | same | 50.1 ± 7.5 | same | |
| (g/kg) | ≤1 | 0.98 ± 0.19 | | 1 ± 0.1 | | 0.8 ± 0.1 | | |

Data are expressed as mean ± standard deviation (SD).
Statistical analysis: repeated measures analysis of variance.
Trend over time: interaction differences in trends between groups.
BMI: body mass index;
ESR: erythrocyte sedimentation rate;
FIM: functional independence measure;
DOSS: Dysphagia Outcome and Severity Scale.
*This amount is the sum of the protein administered/ingested (54.2 g) and protein (6.9 g) provided by supplemented EAAs [41].

The patients also had increased blood concentrations of glucose and normal lactate concentrations. From a functional point of view, – patients had severe disability (FIM –76.7% of normal value). At DOSS evaluation, nineteen patients had severe dysphagia (DOSS=1.21±0.88) and nineteen had a moderate dysphagia (DOSS=3.07±1.76). Daily calories and macronutrients administered or ingested were 22.4±2.7 kcal/kg, 0.94±0.17 g/kg protein, 2.5±0.5 g/kg carbohydrates, 0.98±0.19 g/kg lipids. After randomization, the EAA and Plac sub-groups were similar for all measured variables at baseline.

At discharge, both groups had similar BW reductions, which were not significantly different from the baseline and similar improvements in the rate of dysphagia, physical disability, inflammation, circulating proteins of acute phase response to inflammation. Blood glucose levels improved in the Plac group. Both groups had similar plasma lactate concentrations, which over time did not differ from baseline values. The addition of EAAs 8 g/d EAAs to total protein administered/ingested (54.2 g/d) provided 6.9 g protein substrate, so, at discharge, the treated group had had 1.02 kg protein provided.

The results herein provided confirms that unaffected arm muscles of sub-acute stroke patients may have a prevalence of catabolic over anabolic activity.

The composition herein disclosed tended to improve the rate of inflammation thus converting muscle hypercatabolism (MH) to anabolic/balanced protein metabolism in dysphagic stroke patients at one month after acute event.

Persistent body inflammation, immobilization/disuse, malnutrition were all factors present in the study population that can increase MH in the unaffected arm. The inflammatory status, primed by acute cerebrovascular accident and possibly persisting over time by post-stroke infarction complications, reduces protein synthesis and increases breakdown, also via IL-6 stimulated hypothalamus-pituitary corticosurrenal axis. The rate of proteolysis was probably accentuated by insulin resistance as indicated in the study population by blood glucose concentrations above the normal value. Inflammation was responsible for liver re-prioritization of protein synthesis observed in the study patients.

Disuse, derived from immobilization, de-nervation, muscle unloading, brings about increased proteolysis and, to a lesser extent, reduced protein synthesis.

Unloading per se may lead to muscle proteolysis via induced oxidative stress in skeletal muscle that triggers increased protein degradation.

Post-stroke inadequate nutrition, in particular protein intake, contributes to proteolysis.

The fact that patients had a prolonged inadequate nutritional intake before their admission to rehabilitation is indicated by the associated body weight loss and dysphagia.

The MH finding seems to contrast with the normal levels of patients' circulating essential amino acids. This discrepancy can be reconciled by considering two factors: first, poor nutrition in acute setting would be due to inadequate energy intake but not protein intake, given that the former represents 89.6% of energy body requirements, whereas the latter is 99% of the recommended amount. The amounts of energy and protein ingested were similar to and respectively higher than those reported in a previous study conducted in stroke patients at similar period after acute event (21 d). Normal EAA levels suggest that 1 g/kg/d protein supply to/intake by sub-acute stroke in the rehabilitation stage of the disease may be nutritionally but not metabolically adequate to reduce muscle hypercatabolism. This would suggest that unaffected muscle is a site of profound metabolic perturbations, overriding EAA-promoted anabolic activity.

Disuse, unloading, increased muscle cytokine content are some factors leading to MH. Disuse activates the potent proteolytic activity of ATP-dependent ubiquitin-proteasome pathway, lysosomes, calcium-dependent calpain system. Unloading is a potent promoter of muscle proteolysis via inducing oxidative stress. Increased muscle cytokine content may exert a proteolytic effect, in particular of myofibrillar protein. Interestingly, cytokines affecting muscle cell function can be produced intrinsically within the muscle or by non-muscle cells as neutrophils and macrophages. During inflammation these phagocytes infiltrate the muscular tissue. Other non-resident cells such as fibroblasts, vascular smooth muscle cells, vascular endothelium can produce cytokines.

Besides an adequate protein intake reduced metabolic clearance of circulating BCAAs by the adipose tissue may contribute to normal arterial essential amino acids (EAA) levels. Indeed, adipose tissue modulates the levels of circulating BCAAs but in the case of insulin resistance, as in our study population, reduces or interrupts BCAA uptake.

Previous studies have addressed the timing of post-stroke muscle loss in the unaffected limb. Within the first week of stroke, one study found muscle weakness of unaffected quadriceps of hemiplegic stroke patients and a correlation between a change of quadricep strength and acute weight loss. Another investigation reported no evidence of muscle strength loss in any limb. A number of studies have documented reduced muscle mass and strength six months post-stroke. This was more so in the paretic compared with the non-paretic lower limb and upper limb. A study demonstrated reduced muscle strength in both legs in patients one year after stroke compared to normal subjects.

The results herein reported provides information of the timing of the muscle loss of the unaffected limb as it documents muscle hyper-catabolism in stroke patients one month after stroke. This suggests that, in sub-acute stroke, systemic inflammatory-metabolic alterations may be an important contributor to muscle wasting, adding to other mechanisms of unaffected side weakness. These mechanisms include muscle damage from stroke lesion due to bilateral projections of each cerebral hemisphere, physical inactivity, under-nutrition and possible motor weakness from co-morbidities in pre-event period. It is reasonable to believe that systemic factors also negatively impact the damaged contro-lateral muscles. Compared to healthy subjects, the patients enrolled for the instant study also released significant amounts of the amino acids asparagine, threonine and BCAAs. This would suggest progressive impoverishment of amino acid content of unaffected muscle.

Another finding differentiating stroke and healthy subjects is the concentration of certain amino acids in arterial blood. Strokes have decreased levels of aspartate, asparagine, glutamine, alanine, taurine, tryptophan but increased levels of BCAAs, methionine, phenyl-, lysine. In inflammation and muscle proteolysis, these reductions would suggest increased metabolic clearance of amino acids by visceral organs including liver, gut, kidney, which would be in a hypermetabolic state. For instance, the liver has a high consumption of glyconeogenic aspartate, asparagine, alanine and glutamine, the gut and the kidney of glutamine, the immune cells of glutamine, the brain of all amino acids in particular of the serotonin precursor tryptophan.

The increases in arterial amino acid concentrations are mainly of muscular origin given that, in addition to phenyl-release, BCAAs, methionine, lysine undergoes excessive release. The normal lactate levels suggest that in unaffected arm muscles, there is a balanced aerobic-anaerobic pathway energy-forming Interestingly both protein degradation and synthesis require large amounts of energy in order to occur.

To sum up, this investigation shows that the unaffected arm muscles of hemiplegic, dysphagic stroke patients are sites of hypercatabolic activity which, if not corrected, leads to muscle wasting.

Furthermore, dysphagic strokes have alterations of arterial amino acid profile. The loss of muscle mass and strength has a significant impact on stroke patients' functionality and life prognosis. Muscle depleted subjects have impaired glucose metabolic control, increased risk of osteoporosis, which may be responsible for hip-fracture and falls, cardiovascular de-conditioning and more accentuated disability, in particular walking.

Therefore recognizing and treating muscle wasting as early as possible is of paramount importance for rehabilitation outcome for stroke patients, especially if we consider that 80% of total neuromotor recovery occurs within the first month of acute stroke.

This study clearly indicates that the administration of the composition herein disclosed can correct unaffected muscle protein over-degradation in sub-acute dysphagic stroke patients.

On the contrary, without the administration of such compositions, patients continued to lose muscle mass seventy days after the acute stroke. After rehabilitation, the prevalently anabolic activity in the EAA group was accompanied by unaffected muscle uptake of 49% of arterial amino acids and of plasma total arterial amino acids suggesting the anabolic muscle protein turnover.

This was reinforced by the lower releases of histidine, glycine, taurine compared to those of the Placebo group, as well as by increased arterial TAA availability.

Regarding protein synthesis, essential branched chain amino acids act as fuel and anabolic signals in human muscle. Chronic supplementation of leucine, as here, stimulates post-prandial protein synthesis in responsive tissues including skeletal muscle, liver, adipose tissue. It has been shown that oral intake of 2.5 g leucine stimulates muscle protein synthesis after exercise or an overnight fast.

Regarding proteolysis, leucine is a regulating factor of myofibrillar protein degradation, as it suppresses myofibrillar protein degradation soon after oral administration. Infusion of BCAAs in humans markedly diminishes skeletal muscle protein degradation, but stimulates protein synthesis in the heart. It has been shown that efficient protein use is determined by sensitivity variation of proteolysis to amino acids rather than protein synthesis. Small amounts of amino acids are enough to reduce proteolysis unlike protein synthesis.

Several mechanisms underlie protein synthesis and at the same time, reduce proteolysis by essential amino acids. One mechanism is the adequate availability of essential amino acids per se. Indeed, essential amino acids can stimulate protein synthesis independent of hormones. Other mechanisms include the regulation of gene expression, modulation of anabolic hormone activities, improved aerobic metabolism energy-forming and a reduced circulating TNFα/IGF-1 ratio. Finally, amino acids influence target genes at transcription, mRNA stability and translation Amino acids and in particular EAAs, promote protein synthesis by stimulating insulin-growth factor 1 (IGF-1) and modulating insulin signalling. Indeed, they play a role in regulating insulin signalling via the mTOR nutrient signalling pathway. Insulin (and IGF-1) cannot stimulate protein synthesis if amino acid concentrations are not maintained.

Moreover, essential amino acids can also reduce insulin resistance. Essential amino acids induce anabolic activity indirectly by boosting cell aerobic metabolism to produce energy, the availability of which is indispensable for protein synthesis. Particularly important in a state of systemic inflammation, essential amino acids can promote muscle protein synthesis by reducing circulating cytokine TNFα, so reducing the TNFα/IGF-1 index.

The discrepancy observed here between normal plasma essential amino acids levels and muscle hypercatabolism suggests that chronic supplementation of free essential amino acids may be superior to protein essential amino acids in promoting muscle anabolism. Indeed, for muscle protein synthesis to occur, rapid increases of plasma essential amino acids levels following essential amino acids ingestion is more important than intramuscular amino acid availability. This is because the protein synthetic machinery in muscle is unresponsive after 2.5 hrs. The speed by which blood peak concentrations is achieved is higher after free essential amino acids ingestion than after EAA from protein because the absorption rate of the latter is slowed by the co-presence in the diet of complex carbohydrates and fats.

In addition, the modulation of muscle protein synthesis by blood elevations in essential amino acids may explain why here two stroke-patient groups had similar plasma EAA levels but different muscle protein metabolism responses.

It is imperative that dysphagic stroke subjects are administered adequate amounts of high quality protein. Reduced protein intake leading to low blood essential amino acids levels can contribute to a dramatic increase of MH.

The results herein reported provides useful information for clinical practice since it has been shown that the composition herein disclosed is able attenuate the systemic inflammatory state of stroke patients, and thus convert hypercatabolism to anabolism, which allows a better physical autonomy recovery of the patients.

EXAMPLE 2

Material and Methods

Population. Forty-two dysphagic patients following ischaemic stroke consecutively admitted to the Rehabilitation Institute (Rehab) (Nervi, Genova, Italy) were enrolled within 37±12 days of their acute event.

The patients came from the following origins: stroke units (14.3%), homes (61.9%), neurological settings (23.8%). None of the patients were on steroid therapy, had cancer, nephrotic syndrome, all events that constituted criteria of exclusion of the study in that impacting the reactants of acute-phase response.

Vascular cerebral insult topography was ascertained by computed tomography or magnetic resonance imaging.

The damaged stroke areas were classified in relation to the location of the ischaemic obstruction as PACI (partial anterior circulation infarction; 45.2%), TACI (total anterior circulation infarction; 30.95%), POCI (posterior anterior circulation infarction; 23.8%).

Written informed consent was obtained from participants or whenever relevant from their caregivers, after the nature of the study had been fully explained. The study was approved by the Institutional scientific and ethical committees.

Procedures. Within the first three days of admission to Rehab Institute, the following baseline variables were measured:
  a) anthropometric characteristics: body weight (BW, kg) found using a mechanical weight lifter; height (m), calculated from knee height (Chumlea et al., 1985). Body mass index was calculated as $kg \cdot m^{-2}$. Actual BW was referred to habitual (pre-event) BW. Acutal/habitual BW≤95% was considered a significant loss of BW;
  b) bio-humoral variables: 1) routine variables, including serum protein electrophoresis and the peripheral blood N/Lymph ratio (in the laboratory this ratio in healthy individuals ranges from 1 to 3); 2) biomarkers of body inflammatory status: C-reactive protein (CRP; normal value<0.8 $mg \cdot dl^{-1}$, determined by an immune-turbidimetric method); erythrocyte sedimentation rate (ESR; normal value 2-20 mm at the first hour); 3) acute phase reactants: positive proteins (a-1 globulin system, normal values 210-350 $mg \cdot dl^{-1}$; haptoglobin 30-200 $mg \cdot dl^{-1}$; fibrinogen, normal values 230-550 $mg \cdot dl^{-1}$); negative proteins (albumin, normal values 4.02-4.76 $g \cdot dl^{-1}$; prealbumin, normal values 18-30 $mg \cdot dl^{-1}$ and transferrin, normal values 202-364 $mg \cdot dl^{-1}$);
  c) functional status: evaluated using the Functional Independence Measure (FIM) as elsewhere reported [Keith et al. 1987];
  d) dysphagia: all patients were admitted with a diagnosis of dysphagia. The presence of dysphagia was controlled by the investigators using a video fluoroscopy examination. The severity of dysphagia was evaluated using the Dysphagia Outcome and Severity Scale (DOSS), a 7-point scale developed to systematically rate the functional severity of dysphagia [O'Neil et al 1999]. The score range was 1-7, where level 1 denotes severe dysphagia, level 2 moderately severe dysphagia, level 3 moderate dysphagia, level 4 mild-to-moderate dysphagia, level 5 mild dysphagia, level 6 within functional limit/modified independence and level 7 normal in all situations.
  At admission, 21.4% of the patients were on modified diet, whereas 78.6% were on nasogastric- or percutaneous endoscopic gastrostomy tubes.

Patient randomization. After completing these procedures, patients were randomized to receive essential amino acids (EAAs; EAA group, n=21) or placebo (maltodextrin; placebo group, n=21). A randomization list was generated using SAS statistical software (SAS Institute, Cary, N.C.). A and B were the identifiers of the blinded treatment. The list was made available both to the physician and to hospital pharmacists. The physician sequentially allocated patients to treatment A or B according to the randomization list. The first investigator who interpreted all results was blinded to patients' allocation. The experimental group (EAA group) received 8 g/d of EAAs (Table 2) 4 g in the morning+4 g in the afternoon diluted in half a glass of water. The placebo group was given isocaloric formula containing maltodextrin.

In the patients on artificial nutrition, placebo or EAAs supplementation was given through the feeding tube. In the subjects on modified diet EAAs were given in the form of gelified mixture.

The duration of the treatment (EAAs or maltodextrin) was 35 days. At 38±1 d from admission to rehab the variables from a) to d) were all repeated.

Rehabilitation therapy. All patients followed the centre rehabilitative protocol consisting of performing passive, active and active-assistive range-of-motion exercise coordination, assistive ambulation with devices or support. The duration of treatment by the same therapist was of 60 minutes a day for five days a week. Moreover all patients underwent speech and occupational therapy.

Statistical analysis. All variables were analyzed reporting means and standard deviation for quantitative variables and distribution frequencies for qualitative variables.

Chi-squared test was used for categorical variables. Subsequently, CRP was transformed into natural logarithmic values (ln CRP).

In the entire population, differences in the variables between baseline and discharge values were tested by means of a paired-Student t-test.

The relation between circulating Lymph, N/Lymph ratio and neurofunction test during Rehab were studied by simple correlation analysis.

Patient population was stratified in the group who improved DOSS by at least 1 score and the group with stable DOSS. Baseline differences of the variables between these groups were tested by unpaired t-test. Repeated measurement analysis of variance was used to assess any differences in trends overtime between the two groups of patients.

Linear multiple regression analyses were performed in order to point out the variables with high association with DOSS in the two patient subgroups. Baseline differences in the variables of patients on EAAs and on placebo were tested by unpaired t-test and repeated measurement analysis of variance was used to evaluate differences in trends overtime. Here again, linear multiple regression analyses were carried out in order to point out the variables with high association with DOSS.

The level of statistical significance was set at $p<0.05$.

Results a) Patient Population

Table 8 reports both the patient baseline and discharge demographic-, anthropometric-, biohumoral-, clinical- and neurofunctional characteristics and nutritional intake.

At baseline, the patients had a normal body weight (BW) (BMI=23.7±2.8 kg/m$^2$) but with an average weight loss of 5.3% relative to the pre-stroke BW. The subjects displayed severe losses of physical capacity (FIM: −74% of normal value, on average) and deglutition ability (average DOSS: −71% on average). Moderate and severe dysphagia (DOSS≤3) was observed in 38% of the subjects. Mild systemic inflammation was present (average CRP levels 2.5-fold higher than normal value). The inflammation was associated with reduced levels of the circulating negative proteins (albumin, prealbumin, transferrin) of the acute phase response and with increased serum concentrations of the positive ones (alpha-1 globulin system, haptoglobulin, fibrinogen) and with blood glucose at upper limit of the normal values (Table 8).

At discharge, BW further diminished (average decrease: −1.5 kg, $p<0.02$). This was compatible with significant improvements in both physical disability (average FIM increase: +69%, $p<0.001$) and dysphagia (average DOSS increase: +1.19 score; $p<0.001$). The improvement of dysphagia was noted in 30 patients (71.4%) (16 in placebo and 14 in EAA subjects) whereas stable dysphagia was found in 28.6% patients.

Inflammation was still present but was associated with significant reduced serum levels of anti-protease system (alpha-1 globulin from 311 mg·dl$^{-1}$ to 282 mg·dl$^{-1}$ on average; $p=0.031$), haptoglobin ($p<0.001$) and increased serum concentrations of circulating negative proteins of acute phase response (Table 8). Plasma glucose significantly diminished and normalized ($p=0.008$).

During rehab stay, the subjects who improved and those who did not improve dysphagia developed similar number of infection episodes (1.8±0.4 vs 1.6±0.5, respectively; ns).

TABLE 8

| Variables | normal values | Stroke patients (n = 42) Baseline | Discharge | p level |
|---|---|---|---|---|
| Demographic | | | | |
| Male/Female | — | 27/15 | — | — |
| Age (years) | — | 71 ± 9 | — | — |
| Anthropometric | | | | |
| Actual body weight (kg) | — | 65.4 ± 14.2 | 63.9 ± 13.4 | p = 0.02 |
| Actual/habitual body weight (%) | — | 94.7 ± 6.5 | 92.7 ± 8.9 | p = 0.5 |
| BMI (kg/m$^2$) | — | 23.7 ± 2.8 | 23.1 ± 2.9 | p = 0.6 |
| Blood/serum/plasma | | | | |
| ESR 1$^{st}$ hr (mm) | 2-20 | 46.7 ± 35.2 | 38.2 ± 30.6 | p = 0.2 |
| Haemoglobin (g/dl) | F >12; M >13 | 12.4 ± 1.9 | 12.1 ± 1.2 | p = 0.24 |
| Urea (mg/dl) | 20-40 | 43.9 ± 29.6 | 35.9 ± 14.9 | p = 0.09 |
| Creatinine (mg/dl) | 0.7-1.2 | 0.95 ± 0.29 | 0.94 ± 0.25 | p = 0.76 |
| Glucose (mg/dl) | 80-110 | 109 ± 20.5 | 95 ± 13 | p = 0.008 |
| C-reactive Protein (CRP) (mg/dl) | <0.8 | 2.02 ± 2.4 | 1.33 ± 2.4 | p = 0.17 |
| Fibrinogen (mg/dl) | 230-550 | 433.2 ± 104 | 381 ± 80 | p = 0.001 |
| Haptoglobin (mg/dl) | 30-200 | 267 ± 131.7 | 199.7 ± 92.8 | p < 0.001 |
| α1 globulin (mg/dl) | 210-350 | 311 ± 134 | 282 ± 116 | p = 0.031 |
| Albumin (g/dl) | 4.02-4.76 | 2.89 ± 0.52 | 3.2 ± 0.46 | p < 0.001 |
| Prealbumin (mg/dl) | 18-30 | 17.8 ± 5.1 | 19.5 ± 5.9 | p = 0.058 |
| Transferrin (mg/dl) | 202-364 | 178 ± 32.7 | 195.5 ± 35.8 | p = 0.001 |
| Total White Cells (TWC) (n°/mm$^3$) | 4000-9000 | 7313 ± 2192 | 6086 ± 1632 | p = 0.004 |
| Neutrophils | | | | |
| n°/mm$^3$ | 1800-8000 | 4909 ± 1924 | 3697 ± 1374 | p = 0.001 |
| % TWC | 45-75 | 65.86 ± 10.6 | 59.5 ± 9.3 | p < 0.001 |
| Lymphocytes | | | | |
| n°/mm$^3$ | 700-3700 | 1505 ± 538 | 1688 ± 557 | p = 0.02 |
| % TWC | 20-47 | 21.7 ± 8.9 | 28.6 ± 9.2 | p < 0.001 |
| Neutrophil/Lymphocyte Ratio | 1.5-3.0 * | 3.76 ± 2.07 | 2.43 ± 1.3 | p < 0.001 |
| Neurofunction | | | | |
| FIM score | 125 | 33.02 ± 17.8 | 55.9 ± 26.6 | p < 0.001 |
| DOSS score | 7 | 2.38 ± 1.4 | 3.57 ± 1.59 | p < 0.001 |
| Nutrition (PEG or NT **) | | | | |

TABLE 8-continued

| Variables | normal values | Stroke patients (n = 42) | | |
|---|---|---|---|---|
| | | Baseline | Discharge | p level |
| Energy | | | | |
| (kcal/d) | — | 1350 ± 195 | 1450 ± 210 | p = 0.9 |
| (kcal/kg) | ≥25 | 20.6 ± 1.8 | 22.7 ± 3.4 | p = 0.08 |
| Protein | | | | |
| (g/d) | — | 63.5 ± 8.9 | 62 ± 10.5 | p = 0.2 |
| (g/kg) | >1.1 | 0.971 ± 0.19 | 0.97 ± 0.17 | p = 0.1 |
| Carbohydrates | | | | |
| (g/d) | — | 143 ± 38 | 146 ± 35 | p = 0.1 |
| (g/kg) | 2.5-4 | 2.2 ± 0.4 | 2.3 ± 0.6 | p = 0.2 |
| Lipids | | | | |
| (g/d) | — | 55.4 ± 10 | 56.1 ± 12 | p = 0.15 |
| (g/kg) | <1 | 0.847 ± 0.18 | 0.88 ± 0.2 | p = 0.09 |

Data are expressed as mean ± standard deviation (SD).
Statistical analysis: Paired t student test.
BMI: Body Mass Index;
ESR: Erythrocyte Sedimentation Rate;
FIM: Functional Independence Measure;
DOSS: Dysphagia Outcome and Severity Scale b) Circulating Lymph, N Counts and N/Lymph Ratio Table 8 shows that, at baseline, the patients had normal total white cell (TWC)-, Lymph- and N counts, notwithstanding systemic inflammation, However N/Lymph ratio resulted higher (3.76±2.07) than the normal value of our laboratory (<3).

At discharge, significant reductions of basal TWC (p=0.004) and N (p=0.001) counts were found whereas Lymph count increased (p=0.02). Thus N/Lymph ratio significantly decreased to 2.43±1.3 (p<0.001) and normalized.

c) Relationships Between Circulating Lymph, N/Lymph Ratio and Neurofunction Tests During Rehab Absolute Lymph counts and % Lymph correlated positively with DOSS (r=+0.235, p=0.04 and r=+0.224, p=0.05, respectively) and negatively with inflammation marker ln CRP (r=−0.265, p=0.02 and r=−0.484, p=0.0001 respectively). N counts were positively linked to ln CRP (r=+0.37, p=0.001) and showed a slight negative association with physical ability (FIM, r=−0.20, p=0.07). No correlation was found between N and DOSS. Lymph and N were strongly negatively correlated (r=−0.926, p<0.001). N/Lymph ratio was in inverse relation with physical capacity (r=−0.262, p=0.02) and deglutition ability (r=−0.279, p=0.01) but was positively associated with ln CRP (r=+0.514, p=0.0001). The results show a positive correlation berween FIM and DOSS (r=+0.78, p<0.0001).

In order to better understand the relationship between the overtime changes of circulating immune cells and dysphagia, the entire stroke population was stratified in a first group which, after Rehab, exhibited improved dysphagia (n=30 subjects) and in a second group which did not improve dysphagia (n=12 subjects). Table 9 shows the changes of some variables between subjects with ameliorated and with not ameliorated disphagia.

These variables were simultaneously tested in a logistic regression model finally showing that only % Lymph was significantly associated with improved swallowing capacity (p=0.01). In line with this finding, the overtime changes in % Lymph and DOSS were positively correlated (p=0.015; FIG. 3, panel a).

TABLE 9

| | Overtime changes of dysphagia | | |
|---|---|---|---|
| Variables | Improvement n = 30 | No improvement n = 12 | p value |
| Lymphocytes (% TWC) | +10.35 ± 11.55 | −2.1 ± 12.69 | 0.004 |
| ESR 1$^{st}$ hr (mm) | −14.26 ± 45.92 | +19.27 ± 28.79 | 0.033 |
| C-reactive Protein (CRP) (mg/dl) | −1.22 ± 2.9 | +0.61 ± 2.29 | 0.05 |
| Prealbumin (mg/dl) | +2.22 ± 7.49 | −3.17 ± 8.07 | 0.05 |
| FIM score | +26.7 ± 19.84 | +13.17 ± 15.56 | 0.04 | d) Effects of EAA Supplementation on Lymph and Dysphagia

At baseline, EAA and placebo groups were similar for all the variables considered, except for the serum alpha-1 globulin concentrations higher in placebo than in EAA group (p<0.02) (Table 10). During the rehabilitation period the overtime changes of all the variables considered (Table 11) resulted similar between the two groups of patients except for the alpha-1 globulin that diminished in placebo patients (interaction p=0.01) and for N/Lymph ratio the decrease of which was more pronounced in the EAA group (interaction p=0.04).

TABLE 10

| Variables | Placebo | EAAs | p value |
|---|---|---|---|
| Actual body weight (kg) | 65.63 ± 15.61 | 65.17 ± 13.39 | 1.0 |
| ESR 1$^{st}$ hr (mm) | 59.88 ± 32.0 | 38.54 ± 35.7 | 0.08 |
| Haemoglobin (g/dl) | 12.32 ± 1.61 | 12.41 ± 2.07 | 1.0 |
| Urea (mg/dl) | 42.9 ± 24.8 | 44.78 ± 33.97 | 0.9 |
| Creatinine (mg/dl) | 0.89 ± 0.31 | 0.99 ± 0.28 | 0.7 |
| Glucose (mg/dl) | 108.3 ± 17.3 | 110.3 ± 23.4 | 0.8 |
| C-reactive Protein (CRP) (mg/dl) | 2.21 ± 2.66 | 1.86 ± 2.23 | 0.4 |
| ln (CRP) | 0.28 ± 1.09 | −0.10 ± 1.23 | 0.6 |
| Fibrinogen (mg/dl) | 467.1 ± 121.5 | 405.75 ± 81.01 | 0.5 |
| Haptoglobin (mg/dl) | 306 ± 138.8 | 237.6 ± 121.28 | 0.4 |
| α1 globulin (mg/dl) | 373.3 ± 143.6 | 244.5 ± 87.4 | 0.02 |
| Albumin (g/dl) | 2.83 ± 0.39 | 2.93 ± 0.62 | 0.8 |
| Prealbumin (mg/dl) | 17.5 ± 6.3 | 18.04 ± 4.29 | 0.9 |

TABLE 10-continued

| Variables | Placebo | EAAs | p value |
|---|---|---|---|
| Transferrin (mg/dl) | 181.1 ± 27.99 | 176.0 ± 36.57 | 0.8 |
| Total White Cells (TWC) (n°/mm$^3$) | 7664.3 ± 1814.5 | 7033.5 ± 2464.4 | 0.45 |
| Neutrophils (% TWC) | 66.8 ± 6.9 | 65.09 ± 13.08 | 0.8 |
| Lymphocytes (% TWC) | 20.1 ± 5.8 | 23.11 ± 10.89 | 0.7 |
| Neutrophil/Lymph ratio | 3.68 ± 1.45 | 3.82 ± 1.2 | 0.9 |
| DOSS score | 2.53 ± 1.39 | 2.26 ± 1.48 | 0.8 |
| FIM score | 32.58 ± 15.98 | 33.39 ± 19.46 | 0.9 |

TABLE 11

| Variables | normal values | Placebo Baseline | Placebo Discharge | EAAs Baseline | EAAs Discharge | p level |
|---|---|---|---|---|---|---|
| Demographic | | | | | | |
| Male/Female | — | 15/6 | — | 12/9 | — | — |
| Age (years) | — | 73.5 ± 8.6 | — | 67.5 ± 10.5 | — | — |
| Anthropometric | | | | | | |
| Actual body weight (kg) | — | 65.63 ± 15.61 | 64.1 ± 15.1 | 65.17 ± 13.39 | 63.83 ± 12.14 | p = 0.2 |
| Actual/habitual body weight (%) | — | 93.8 ± 7.5 | 93.6 ± 9 | 95.9 ± 5.8 | 92.9 ± 8.9 | p = 0.3 |
| BMI (kg/m$^2$) | — | 24.8 ± 3.2 | 23.2 ± 3 | 22.7 ± 2.6 | 23.1 ± 2.9 | p = 0.2 |
| Blood/serum/plasma | | | | | | |
| ESR 1$^{st}$ hr (mm) | 2-20 | 59.88 ± 32.0 | 39.7 ± 26.5 | 38.54 ± 35.7 | 37.18 ± 33.9 | p = 0.2 |
| Haemoglobin (g/dl) | F > 12; M > 13 | 12.32 ± 1.61 | 12.1 ± 0.98 | 12.41 ± 2.07 | 12.03 ± 1.35 | p = 0.9 |
| Urea (mg/dl) | 20-40 | 42.9 ± 24.8 | 34.4 ± 13.2 | 44.78 ± 33.97 | 37.17 ± 16.46 | p = 0.8 |
| Creatinine (mg/dl) | 0.7-1.2 | 0.89 ± 0.31 | 0.95 ± 0.28 | 0.99 ± 0.28 | 0.93 ± 0.23 | p = 0.09 |
| Glucose (mg/dl) | 80-110 | 108.3 ± 17.3 | 97.7 ± 4.1 | 110.3 ± 23.4 | 93.1 ± 12.11 | p = 0.5 |
| C-reactive Protein (CRP) (mg/dl) | <0.3 | 2.21 ± 2.66 | 1.28 ± 2.12 | 1.86 ± 2.23 | 1.37 ± 2.74 | p = 0.7 |
| ln CRP | | 0.28 ± 1.09 | −0.62 ± 1.32 | −0.10 ± 1.23 | −0.78 ± 1.25 | p = 0.7 |
| Fibrinogen (mg/dl) | 230-550 | 467.1 ± 121.5 | 392.1 ± 74.5 | 405.75 ± 81.01 | 372.38 ± 85.85 | p = 0.8 |
| Haptoglobin (mg/dl) | 30-200 | 306 ± 138.8 | 233.7 ± 90.5 | 237.6 ± 121.28 | 174.2 ± 88.24 | p = 0.6 |
| α1 globulin (mg/dl) | 210-350 | 373.3 ± 143.6 | 314.2 ± 133 | 244.5 ± 87.4 | 247.3 ± 87.9 | P = 0.01 |
| Albumin (g/dl) | 4.02-4.76 | 2.83 ± 0.39 | 3.18 ± 0.39 | 2.93 ± 0.62 | 3.28 ± 0.52 | p = 0.6 |
| Prealbumin (mg/dl) | 18-30 | 17.5 ± 6.3 | 18.6 ± 5.1 | 18.04 ± 4.29 | 20.3 ± 6.3 | p = 0.8 |
| Transferrin (mg/dl) | 202-364 | 181.1 ± 27.99 | 195.5 ± 33.5 | 176.0 ± 36.57 | 195.56 ± 38.51 | p = 0.9 |
| Total White Cells (TWC) (n°/mm$^3$) | 4000-9000 | 7664.3 ± 1814.5 | 6404.4 ± 1446.1 | 7033.5 ± 2464.4 | 5832.5 ± 1762.6 | p = 0.3 |
| Neutrophils | | | | | | |
| n°/mm$^3$ | 1800-8000 | 5182.95 ± 1605.1 | 3979.99 ± 1359.4 | 4678.79 ± 2174.35 | 3459.08 ± 1377.34 | p = 0.5 |
| % TWC | 45-75 | 66.8 ± 6.9 | 61.3 ± 8.4 | 65.09 ± 13.08 | 57.92 ± 9.97 | p = 0.7 |
| Lymphocytes | | | | | | |
| n°/mm$^3$ | 700-3700 | 1502.98 ± 485.5 | 1702.88 ± 504.44 | 1506.83 ± 592.31 | 1675.71 ± 612.61 | p = 0.7 |
| % TWC | 20-47 | 20.1 ± 5.8 | 27.3 ± 8.0 | 23.11 ± 10.89 | 29.67 ± 10.1 | p = 0.6 |
| Neutrophil/Lymph Ratio | 1.5-3.1 | 3.68 ± 1.45 | 2.60 ± 1.46 | 3.82 ± 1.2 | 2.30 ± 1.18 | p = 0.04 |
| Neurofunction | | | | | | |
| FIM score | 125 | 32.58 ± 15.98 | 57.37 ± 29.34 | 33.39 ± 19.46 | 54.65 ± 24.81 | p = 0.8 |
| DOSS score | 7 | 2.53 ± 1.39 | 4.05 ± 1.39 | 2.26 ± 1.48 | 3.17 ± 1.66 | p = 0.1 |
| Nutrition | | | | | | |
| Energy | | | | | | |
| (kcal/d) | — | 1405 ± 205 | 1557 ± 206 | 1355 ± 189 | 1472 ± 215 | p = 0.9 |
| (kcal/kg) | ≥25 | 21.3 ± 2.1 | 24.4 ± 3.9 | 20.6 ± 1.5 | 23.0 ± 3.05 | p = 0.9 |
| Protein | | | | | | |
| (g/d) | — | 62 ± 7.9 | 61.5 ± 8.5 | 64.9 ± 9.1 | 62.8 ± 11.4 | p = 0.8 |
| (g/kg) | >1.1 | 0.942 ± 10.2 | 0.964 ± 0.19 | 0.99 ± 0.18 | 0.98 ± 0.16 | p = 0.7 |
| Carbohydrates | | | | | | |
| (g/d) | — | 150 ± 41 | 148 ± 39 | 138 ± 35 | 149.5 ± 31.1 | p = 0.2 |
| (g/kg) | 2.5-4 | 2.28 ± 0.5 | 2.32 ± 0.7 | 2.1 ± 0.3 | 2.33 ± 0.5 | p = 0.8 |

TABLE 11-continued

| Variables | normal values | Placebo | | EAAs | | p level |
| --- | --- | --- | --- | --- | --- | --- |
| | | Baseline | Discharge | Baseline | Discharge | |
| Lipids | | | | | | |
| (g/d) | — | 50.7 ± 8.5 | 51.5 ± 10.9 | 60.1 ± 11.3 | 60.5 ± 12.8 | p = 0.5 |
| (g/kg) | <1 | 0.77 ± 0.2 | 0.81 ± 0.19 | 0.916 ± 0.16 | 0.944 ± 0.21 | p = 0.7 |

Values are expressed as mean ± standard deviation.
Statistical analysis: Repeated measure analysis of variance.
The p level of the interaction term (time * treatment) is reported only.
Level of significance set at p < 0.05

In both groups the improvements of dysphagia were positively linked to improvements in % Lymph (FIG. 3, panels b and c) but the association was more evident in the EAA group suggesting that the association observed in the entire stroke population (FIG. 3, panel a) is mainly ascribed to EAA treatment.

The study shows that during the subacute stage of ischemic stroke the patients at admission to Rehab Institute had normal peripheral blood Lymph and N counts but high N/Lymph ratio. After rehab, N/Lymph ratio normalized because of decreased N count and increased Lymph count. Furthermore, the study shows that increased peripheral blood % Lymph is significantly associated with improved dysphagia disability and that this relationship is potentiated by supplementing essential amino acids (EAAs) to patients.

1) Circulating Lymph- and N Counts, N/Lymph Ratio

The study indicates a normal profile of blood total white cells, Lymph and N counts with mildly increased N/Lymph ratio.

During Rehab a decline of post acute inflammation rate with positive impact on patient clinical-metabolic status occurred. In fact, the reduction in N/Lymph ratio was associated with patient improvements in physical and swallowing disabilities, circulating levels of the negative proteins of acute phase response, potentially influencing cerebral repair. Moreover the patients improved plasma glucose concentration, indicating a reduction of insulin resistance state.

The blood profile of immune cells during subacute stroke is the opposite to that described in acute or immediately post-acute phase of cerebral ischemia. In acute ischemia total white cells and N count are increased and Lymph count is decreased and within days of the stroke, the inhibition of Lymph proliferation/activity occurs because of both suppressive effect by overactivated autonomic nervous system on spleen and lymphonodes and direct inhibitory activity exerted by N on Lymph.

In contrast to acute stage of stroke in which the reduction of adaptive immune system is beneficial for the patients, during subacute stroke the amelioration of adaptive immune system not only is not detrimental but also may foster neuroregeneration. The findings of the present study documents that the restoration of immune system function was accompanied by improvement in FIM both in stroke and spinal cord injury patients.

It is possible that the increase of circulating Lymph observed in subacute patients could be due to reduced corticosteroid production following reduced inflammation rate, as elevated corticosteroid (and metanephrine) levels are associated with lymphopenia after extensive brain infarction. Lymphocytes express more glucocorticoid receptors than granulocytes and monocytes. The blockade of these receptors prevents lymphopenia. Even though circulating corticosteroid levels were not determined in the current study, the normalization of blood glucose during rehab, indicating reduced insulin resistance, suggests a reduction of corticosteroid production. As in acute ischemia Ns influence the stroke severity, the decline of Ns during rehab could favour the processes of neurorepair and neuroregeneration. In the present study, this is indirectly suggested by the negative correlation found between N/Lymph ratio and the retrievals of both physical (FIM) and deglutition (DOSS) disabilities. This suggests that the lower the inflammation, the higher the deglutition ability.

Even if innate and adaptive immune systems mutually cooperate to ensure the best immunological response after cerebral ischemia-induced inflammation, Ns and Lymphs are inversely correlated because Ns can inhibit Lymph number and activity.

In synthesis, the study suggests that during subacute stroke the adaptive immunity may be predominant on the innate immune system and may be associated with patient neurofunction retrieval whereas the persistence of higher rate of inflammation may be prejudicial for deglutition retrieval.

2) EAA Supplementation and the Relationship Between Adaptive Immune System and Neurofunction The study shows that EAAs are associated with significant reduction of blood N/Lymph ratio and enhancement of the relation between the improved time courses of % Lymph and DOSS. Thus EAAs influence both blood immunity and neurorepair processes. Given the metabolic activity of EAAs, these substrates promote these processes in virtue of several mechanisms.

Firstly, EAAs can directly induce protein synthesis in immune cells for Lymph proliferation and duplication.

When Ns are prevalent over Lymphs, as in acute ischemia and at admission phase of patients to rehab, the phagocytic activity of circulating N may negatively impact the retrieval of deglutition. In the present study, this is highlighted by the negative correlation found between N/Lymph ratio and deglutition capacity. Thus the study suggests that EAAs change the immunity profile in favour of adaptive immunity over the inflammatory pattern.

Secondly, EAA-induced protein synthesis directly improves the deglutition capacity by impacting the mechanisms underlying normal deglutition such as interneuronal activity and/or deglutition center and/or peripheral neuromuscular function of deglutition.

Thirdly, EAA-induced body anabolic status is of paramount importance for brain remodelling and function. In the study, the improved anabolic status, notwithstanding a slight loss of baseline body weight, was denoted by the restoration of hepatic synthesis of the negative proteins of acute phase response such as albumin, transferrin, prealbumin. Of note, these proteins per se may play a role in brain repair/regeneration and reactivation of neural networks.

The study shows that more than 28% of the patients did not improve dysphagia during rehab. This could be due to the absence of cortical excitability in the undamaged hemisphere. This hypothesis relies on the following: 1) swallowing musculature is represented in each hemisphere but with marked interhemispheric asymmetry; 2) the occurrence of dysphagia is related to the size of the pharyngeal projection in the intact hemisphere.

The study shows that physical (FIM) and deglutition (DOSS) abilities are interrelated. The fact that at the logistic regression analysis, the dysphagia outcome was mainly associated with % Lymph and not with FIM suggests that the improvement in dysphagia is dependent not only on general improvement of neural networks, like in placebo individuals, but is also mediated by increased activity of adaptive immune system on cerebral remodelling, like in EAA patients.

Moreover, the experimental data highlight the presence of a positive correlation between the value of N/Lymph ratio and the concentration of EAAs in arterial blood, mainly the branched essential amino acids (leucine, isoleucine and valine).

On the contrary, the correlations between the value of N/Lymph ratio and the total concentration of amino acids in arterial blood as well as the correlation between the value of N/Lymph ratio and the total concentration of amino acids in venous blood are not significant.

The physiopathological explanation of the above lies in the fact that the higher the inflammatory processes (high N/Lymph ratio) are the higher the multidistrict protein turn-over (high amounts of protein mediators of inflammation, eg cytokines, are synthesized) and therefore the higher the need to have an adequate concentration, especially of essential amino acids in the systemic arterial bloodstream, for protein synthesis, while the venous blood reflects the flow from muscle catabolism.

REFERENCES

1. R. Aquilani, M. Boselli, P. Baiardi, et al., "Is stroke rehabilitation a metabolic problem?" *Brain Inj*, vol. 28, no. 2, pp. 161-173, 2014.
2. R. Aquilani, M. T. La Rovere, O. Febo, et al., "Preserved muscle protein metabolism in obese patients with chronic heart failure" *Int J Cardiol*, vol. 160, no. 2, pp. 102-108, 2012.
3. Z. Liu and E. J. Barrett, "Human protein metabolism: its measurement and regulation" *Am J Physiol Endocrinol Metab*, vol. 283, no. 6, pp. E1105-E1112, 2002.
4. W. C. Chumlea, A. F. Roche, and M. L. Steinbaugh, "Estimating stature from knee height for persons 60 to 90 years of age" *J Am Geriatr Soc*, vol. 33, no. 2, pp. 116-120, 1985.
5. R. A. Keith, C. V. Granger, B. B. Hamilton, and F. S. Sherwin, "The functional independence measure: a new tool for rehabilitation" In: M. G. Eisenberg, R. C. Grzesiak, eds. *Advances in Clinical Rehabilitation*, Vol. I. New York: Springer-Verlag, pp. 6-18, 1987.
6. K. H. O'Neil, M. Purdy, J. Falk, and L. Gallo, "The Dysphagia Outcome and Severity Scale" *Dysphagia*, vol. 14, no. 3, pp. 139-145, 1999.
7. E. Carnevale and L. Marletta. Istituto Nazionale di Ricerca per gli Alimenti e la Nutrizione, INRAN. Tabelle di composizione degli alimenti. Roma, Italy: Istituto Superiore Nazionale della Nutrizione; 1989.
8. R. Aquilani, R. Tramarin, R. F. Pedretti, et al., "Despite good compliance, very low fat diet alone does not achieve recommended cholesterol goals in outpatients with coronary heart disease" *Eur Heart J*, vol. 20, no. 14, pp. 1020-1029, 1999.

The invention claimed is:

1. A method for treatment of a systemic inflammation state associated with a stroke in a patient with dysphagia, said method comprising administering to the patient an amino acid composition comprising an active agent, said active agent consisting of the amino acids leucine, isoleucine, valine, lysine, threonine, histidine, phenylalanine, methionine, tryptophan, tyrosine, and cystine,
   wherein the composition further comprises one or more thickener agents in an amount between 10% and 50% by weight, and
   wherein the composition is free of any amino acids other than said leucine, isoleucine, valine, lysine, threonine, histidine, phenylalanine, methionine, tryptophan, tyrosine, and cystine.

2. The method according to claim 1, wherein the thickener agents are selected from xanthan gum, methylhydroxypropylcellulose, konjak gum, konjak glucomannan, gum Arabic (Acacia gum), and modified starches.

3. The method according to claim 1, wherein the leucine:isoleucine:valine weight ratio is equivalent to 2:1:1.

4. The method according to claim 1, wherein
   the isoleucine:leucine weight ratio is in the range 0.2-0.7, and/or
   the valine:leucine weight ratio is in the range 0.2-0.8.

5. The method according to claim 1, wherein
   the threonine:leucine weight ratio is in the range of 0.15-0.50, and/or
   the lysine:leucine weight ratio is in the range of 0.15-0.60.

6. The method according to claim 1, wherein the composition further comprises one or more vitamins.

7. The method according to claim 1, wherein the composition further comprises carbohydrates, additives and/or flavouring substances.

8. The method according to claim 1, wherein
   the isoleucine:leucine weight ratio is in the range 0.4-0.6, and/or
   the valine:leucine weight ratio is the range 0.4-0.7.

9. The method according to claim 1, wherein
   the threonine:leucine weight ratio is in the range of 0.20-0.45, and/or
   the lysine:leucine weight ratio is in the range of 0.30-0.55.

10. The method according to claim 6, wherein the vitamins are selected from the group of B vitamins.

11. The method according to claim 6, wherein the vitamins are vitamin $B_1$ and/or vitamin $B_6$.

12. The method according to claim 10, wherein the B vitamins are vitamin $B_1$ and/or vitamin $B_6$.

* * * * *